(12) United States Patent
Alles et al.

(10) Patent No.: US 7,158,284 B2
(45) Date of Patent: Jan. 2, 2007

(54) APPARATUS AND METHODS OF USING SECOND HARMONIC GENERATION AS A NON-INVASIVE OPTICAL PROBE FOR INTERFACE PROPERTIES IN LAYERED STRUCTURES

(75) Inventors: Michael Lee Alles, Nashville, TN (US);
Norman H. Tolk, Brentwood, TN (US);
Bongim Jun, Nashville, TN (US);
Robert Pasternak, Nashville, TN (US);
Ron Schrimpf, Franklin, TN (US);
Sorin Cristoloveanu, Seyssinet-Pariset (FR)

(73) Assignee: Vanderbilt University, Nashville, TN (US)

( * ) Notice: Subject to any disclaimer, the term of this patent is extended or adjusted under 35 U.S.C. 154(b) by 119 days.

(21) Appl. No.: 11/019,906

(22) Filed: Dec. 21, 2004

(65) Prior Publication Data
US 2006/0044641 A1    Mar. 2, 2006

Related U.S. Application Data

(63) Continuation-in-part of application No. 10/976,358, filed on Oct. 28, 2004, now abandoned, which is a continuation-in-part of application No. 10/363,347, filed on Sep. 15, 2003.

(60) Provisional application No. 60/518,827, filed on Nov. 10, 2003, provisional application No. 60/125,002, filed on Mar. 18, 1999.

(51) Int. Cl.
*G02F 1/37* (2006.01)
*G01R 31/308* (2006.01)

(52) U.S. Cl. ...................... 359/328; 324/752

(58) Field of Classification Search ............... 359/326, 359/328, 329; 324/752
See application file for complete search history.

(56) References Cited

U.S. PATENT DOCUMENTS

| | | | |
|---|---|---|---|
| 4,758,092 A | 7/1988 | Heinrich et al. | 356/364 |
| 5,283,141 A | 2/1994 | Yoon et al. | 430/30 |
| 5,416,337 A | 5/1995 | Chang et al. | 257/13 |
| 5,500,188 A | 3/1996 | Hafeman et al. | 204/403.01 |
| 5,519,334 A | 5/1996 | Dawson | 324/765 |
| 5,559,428 A | 9/1996 | Li et al. | 324/71.5 |
| 5,705,831 A | 1/1998 | Uemura et al. | 257/78 |
| 5,750,981 A | 5/1998 | Fonash | 250/214 R |
| 5,770,946 A | 6/1998 | Patterson | 324/752 |
| 5,867,034 A | 2/1999 | Sokolov et al. | 324/765 |
| 5,872,360 A | 2/1999 | Paniccia et al. | 250/341.4 |
| 6,587,258 B1 * | 7/2003 | Kane | 359/328 |

(Continued)

OTHER PUBLICATIONS

Aktsipetrov et al, "Optical Second-Harmonic Generation Induced By A DC Electric Field At The Si-SiO2 Interface", Optics Letters, vol. 19, No. 18, Sep. 15, 1994, pp. 1450-1452.*

(Continued)

*Primary Examiner*—John D. Lee
(74) *Attorney, Agent, or Firm*—Morris Manning & Martin LLP; Tim Tingkang Xia, Esq.

(57) ABSTRACT

A method for non-invasively probing at least one interface property in a layered structure having at least one interface. In one embodiment, the method includes the steps of exposing the layered structure to an incident photon beam at an incident angle to produce a reflection beam, measuring intensities of the second harmonic generation signals from the reflection beam, and identifying an initial second harmonic generation intensity and a time evolution of second harmonic generation intensity from the measured second harmonic generation intensities so as to determine the at least one interface property of the layered structure.

42 Claims, 12 Drawing Sheets

U.S. PATENT DOCUMENTS 6,856,159 B1 * 2/2005 Tolk et al. ............. 324/765

OTHER PUBLICATIONS

Meyer et al, "Electronic Transitions At Si(111)/SiO2 And Si(111)/Si3N4 Interfaces Studied By Optical Second-Harmonic Spectroscopy", Physical Review Letters, vol. 74, No. 15, Apr. 10, 1995, pp. 3001-3004.*

Lüpke et al, "Optical Second-Harmonic Generation As A Probe Of Electric-Field-Induced Perturbation Of Centrosymmetric Media", Optics Letters, vol. 20, No. 19, Oct. 1, 1995, pp. 1997-1999.*

Bjorkman, C. J. et al., "Influence Of Surface Roughness On The Electrical Properties Of Si-$Sio_2$ Interfaces And On Second-Harmonic Generation At These Interfaces," *J. Vac. Sci. Technol. B*, vol. 11, (1993) p. 1521-1527.

Bloch, J. et al., "Electron Photoinjection from Silicon to Ultrathin $SiO_2$ Films via Ambient Oxygen" *Phys. Rev. Lett.*, vol. 77, (1996) p. 920-923.

Bratu, P. et al., "Kinetics Of Oxygen Dissociation On Si(111)7×7 Investigated With Optical Second-Harmonic Generation," *Phys. Rev. B*, vol. 49, (1994) p. 14070-14073.

Cristoloveanu, S. et al., "A Review of the Pseudo-MOS Transistor in SOI Wafers: Operation, Parameter Extraction, and Applications," *Trans. Electron Dev.* vol. 47, No. 5, (2000) p. 1018-1027.

Cundiff, S. T. et al., "Second-Harmonic Generation At The Interface Between Si(100) And Thin $Sio_2$ Layers," *J. Vac. Sci. Technol. A*, vol. 16, (1998) p. 1730-1734.

Dadap, J. et al., "Randomly Oriented Angstrom-Scale Microroughness At The Si(100)/$SiO_2$ Interface Probed By Optical Second Harmonic Generation," *Appl. Phys. Lett.*, vol. 64, (1994) p. 2139-2141.

Engel, T. "The Interaction Of Molecular And Atomic Oxygen With Si(100) and Si(111)" *Surf. Sci. Rep.* vol. 18, (1993) p. 91-144.

Govorkov, S. V. et al., "Inhomogeneous Deformation Of Silicon Surface Layers Probed By Second-Harmonic Generation In Reflection," *J. Opt. Soc. Am. B*, vol. 6, (1989) p. 1117-1124.

Heinz, T. F., et al., "Study of symmetry and disordering of Si(111)-7×7 surfaces by optical second harmonic generation," *J. Vac. Sci. Technol. B*, vol. 3, (1985) p. 1467-1470.

Jun, B. et al., "Characterization Of Multiple Si/Sio2 Interfaces In Silicon-On-Insulator Materials Via Second-Harmonic Generation," *Appl. Phys. Lett.*, vol. 85, No. 15, (2004) p. 3095-3097.

Jun, B. et al., "Charge Separation Techniques for Irradiated Pseudo-MOS SOI Transistors," *IEEE Trans. Nucl. Sci.* vol. 50, No. 6, (2003) p. 1891-1895.

Jun, B. et al., "Charge Trapping in Irradiated SOI Wafers Measured by Second Harmonic Generation," *IEEE Trans. Nucl. Sci.*, vol. 51, No. 6, (2004) p. 3231-3237.

Nakamura, K. et al., "Comparison Of Initial Oxidation Of Si(111)7×7 With Ozone And Oxygen Investigated By Second Harmonic Generation," *J. Vac. Sci. Technol. A*, vol. 15, (1997) p. 2441-2445.

Perakis, I. E. et al., "Many-Body Correlation Effects in the Ultrafast Non-Linear Optical Response of Confined Fermi Seas" *Surf. Sci. Rep.* (2000) vol. 40, p. 1-74.

Shklyaev, A. A. et al., "Branching of Critical Conditions for Si(111)-(7×7) Oxidation," *Phys. Rev. Lett.* vol. 75, (1995) p. 272-275.

Tom, H. W. K. et al., "Investigation Of The Si(111)-(7×7) Surface By Second-Harmonic Generation: Oxidation And The Effects Of Surface Phosphorus," *Surf. Sci.* (1986) p. 167-176.

* cited by examiner (a)

(b)

(a)

(b)      (c)      (d)

APPARATUS AND METHODS OF USING SECOND HARMONIC GENERATION AS A NON-INVASIVE OPTICAL PROBE FOR INTERFACE PROPERTIES IN LAYERED STRUCTURES

CROSS-REFERENCE TO RELATED PATENT APPLICATION

This application is a continuation-in-part of U.S. patent application Ser. No. 10/363,347, filed Sep. 15, 2003, entitled "CONTACTLESS OPTICAL PROBE FOR USE IN SEMICONDUCTOR PROCESSING METROLOGY," by Norman H. Tolk, Owner Luepke, and Wei Wang, the disclosure for which is hereby incorporated herein by reference in its entirety, which is now issued as U.S. Pat. No. 6,856,159 and itself claims the benefit, pursuant to 35 U.S.C. §119(e), of provisional U.S. patent application Ser. No. 60/125,002, filed Mar. 18, 1999, entitled "CONTACTLESS OPTICAL PROBE FOR USE IN SEMICONDUCTOR PROCESSING METROLOGY," by Norman H. Tolk, Gunter Luepke, and Wei Wang, which is incorporated herein by reference in its entirety. This application also is a continuation-in-part of U.S. patent application Ser. No. 10/976,358, filed Oct. 28, 2004, now abandoned entitled "APPARATUS AND METHODS OF USING ULTRA FAST SPIN DYNAMICS IN SEMICONDUCTOR HETEROSTRUCTURES PROBED BY SECOND HARMONIC GENERATION" by Norman H. Tolk, Yuri D. Glinka, T. V. Sbahbazyan, and I. E. Perakis, the disclosure for which is hereby incorporated herein by reference in its entirety, which status is pending and itself claims the benefit, pursuant to 35 U.S.C. §119(e), of provisional U.S. patent application Ser. No. 60/518,827, filed Nov. 10, 2003, entitled "APPARATUS AND METHODS OF USING ULTRA FAST SPIN DYNAMICS IN SEMICONDUCTOR HETEROSTRUCTURES PROBED BY SECOND HARMONIC GENERATION," by Yuri D. Glinka, T. V. Sbahbazyan, I. E. Perakis, and Norman H. Tolk, which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [11] represents the 11th reference cited in the reference list, namely, R. Pasternak, Y. V. Shirokaya, Z. Marka, J. K. Miller, S. N. Rashkeev, S. T. Pantelides, N. H. Tolk, B. K. Choi, R. D. Schrimpf, and D. M. Fleetwood, "Laser detection of radiation enhanced electron transport in ultra-Thin oxides," *Nuclear Instruments and Methods in Physics Research Sec. A*. vol. 514, pp. 150–155, 2003.

STATEMENT OF FEDERALLY-SPONSORED RESEARCH

The present invention was made with Government support under a contract F49620-99-1-0289 awarded by Air Force Office of Scientific Research, and by Office of Naval Research. The United States Government may have certain rights to this invention pursuant to these grants.

FIELD OF THE INVENTION

The present invention generally relates to layered structures and in particular to the utilization of second harmonic generation as a non-invasive optical probe for at least one interface property of the layered structures.

BACKGROUND OF THE INVENTION

Metal-oxide semiconductor (hereinafter "MOS") transistors fabricated on silicon-on-insulator (hereinafter "SOI") wafers have received great attention because of advantages in device isolation, speed, density, and scalability over bulk silicon devices [1]. Although SOI devices are naturally resistant to transient photocurrents and single event upset, total-dose irradiation may induce a parasitic conduction path at the buried oxide (hereinafter "BOX") interface due to radiation-induced oxide and interface traps [2]. On the other hand, it has been noted that with ever decreasing SOI thickness for future generation of the complementary metal-oxide semiconductor (hereinafter "CMOS") technology, there will be a negative impact on carrier mobility in the channel because of the proximity of the Si/BOX interface to the gate (commonly $SiO_2$). In addition, dopants may penetrate from the heavily doped polysilicon gate into the substrate, which causes instability in the threshold voltage. The performance and reliability of MOS structures depends more and more on the microscopic quality of dielectrics and their interfaces. Thus, characterization of these interfaces will be of increasing importance. Conventionally, the properties of the buried layer and interfaces of the SOI wafers have been investigated by means of destructive, non-real-time methods with limited sampling frequency, such as electrical characterization including current-voltage (hereinafter "I-V") and capacitance-voltage (hereinafter "C-V") measurements on patterned capacitor structures, point contact transistor measurements, and mercury probe measurements, etc., or physical measurements including atomic force microscopy following selective chemical etching. Wafer-level measurements via the pseudo-MOS technique are frequently used for evaluation of partially-processed wafers [3–5].

One of drawbacks of these destructive, non-real-time methods is that it damages the active device regions by directly probing the Si-film of the device, and it is limited to characterization of the top $Si/SiO_2$ interface of the device.

Therefore, a heretofore unaddressed need still exists in the art to address the aforementioned deficiencies and inadequacies.

SUMMARY OF THE INVENTION

The present invention, in one aspect, relates to a method for non-invasively probing at least one interface property of a layered structure. The layered structure at least includes a silicon substrate and an oxide layer deposited on the silicon substrate to form a first $Si/SiO_2$ interface therebetween. In one embodiment, the layered structure further has a silicon layer deposited on the oxide layer to form a second $Si/SiO_2$ interface therebetween. The at least one interface property of the layered structure includes at least one of interface roughness, interface state density, trapped charge density, surface recombination velocity, electrically active impurity, and interface morphology. In one embodiment, the method includes the step of exposing the layered structure to an incident photon beam at an incident angle to produce a reflection beam. The incident photon beam redistributes carriers across the first Si/SiO$_2$ interface and induces an electric field at the first Si/SiO$_2$ interface. In one embodiment, the incident photon beam includes substantially monochromatic electromagnetic radiation, where the substantially monochromatic electromagnetic radiation comprises a laser beam. The laser beam can be a pulsed laser beam. The reflection beam has a fundamental mode of the incident photon beam and SHG signals.

The method further includes the steps of optically separating the SHG signals from the reflection beam and measuring intensities of the SHG signals. In one embodiment, the optically separating step is performed with a prism. The measuring step has the step of detecting the SHG signals by a photomultiplier tube. In one embodiment, the intensities of the SHG signals are measured with a photon counter.

Moreover, the method includes the step of identifying an initial SHG intensity and a time evolution of the SHG intensity from the measured SHG intensities so as to determine the at least one interface property of the layered structure. The initial SHG intensity includes a contribution of the incident photon beam to the second harmonic generation, and differences between the measured SHG intensities and the initial SHG intensity include a contribution of the induced electric field at the first Si/SiO$_2$ interface to the second harmonic generation.

Furthermore, the method includes the step of blocking the incident photon beam off the layered structure at a predetermined time for a predetermined period of time. Additionally, the method includes the step of applying a bias electric field to the layered structure. The bias electric field, in one embodiment, has a DC electric field.

In another aspect, the present invention relates to a method for non-invasively probing at least one interface property of a layered structure, wherein the layered structure at least includes a first layer and a second layer having physics properties substantially different from that of the first layer, the second layer deposited on the first layer to form an interface therebetween. The interface comprises one of a semiconductor/dielectric interface, a semiconductor/semiconductor interface, a metal/insulator interface, and a metal/dielectric interface. The at least one interface property of the layered structure comprises at least one of interface roughness, interface state density, trapped charge density, surface recombination velocity, electrically active impurity, and interface morphology.

In one embodiment, the method has the step of exposing the layered structure to an incident photon beam at an incident angle to produce a reflection beam, where the incident photon beam redistributes carriers across the interface and induces an electric field at the interface, and the reflection beam includes a fundamental mode of the incident photon beam and SHG signals. Furthermore, the method has the steps of measuring intensities of the SHG signals from the reflection beam, and identifying an initial SHG intensity and a time evolution of the SHG intensity from the measured SHG intensities so as to determine the at least one interface property of the layered structure. The initial SHG intensity includes a contribution of the incident photon beam to the second harmonic generation, and differences between the measured SHG intensity and the initial SHG intensity include a contribution of the induced electric field at the interface to the second harmonic generation.

Moreover, the method has the step of blocking the incident photon beam off the layered structure at a predetermined time for a predetermined period of time. Additionally, the method has the step of applying a bias electric field to the layered structure, where the bias electric field has a DC electric field.

In yet another aspect, the present invention relates to a non-invasive optical probe for at least one interface property of a layered structure. The layered structure at least has a first layer and a second layer having physics properties substantially different from that of the first layer, where the second layer is deposited on the first layer to form an interface therebetween. The interface includes one of a semiconductor/dielectric interface, a semiconductor/semiconductor interface, a metal/insulator interface, and a metal/dielectric interface.

In one embodiment, the non-invasive optical probe includes a light source for emitting a light beam incident to the layered structure to produce a reflection beam, optical means for separating SHG signals from the reflection beam, and a detector for measuring intensities of the SHG signals. The reflection beam has a fundamental mode of the incident photon beam and SHG signals. The measured SHG signal intensities are associated with the at least one interface property of the layered structure. The detector, in one embodiment, includes a photomultiplier tube. In one embodiment, the light source includes a laser.

The non-invasive optical probe further includes a source of an electric field for generating a bias field applied to the layered structure. In one embodiment, the first layer of the layered structure is made of silicon. The second layer of the layered structure is made of oxide. The layered structure may further include a silicon layer deposited on the second layer of the layered structure.

In a further aspect, the present invention relates to a non-invasive optical probe for at least one interface property of a layered structure having at least one interface, where the at least one interface includes one of a semiconductor/dielectric interface, a semiconductor/semiconductor interface, a metal/insulator interface, and a metal/dielectric interface. In one embodiment, the method has a laser source emitting a beam of pulses that is directed into the layered structure to induce SHG signals, and an optical system for measuring intensities of the induced SHG signals. The measured SHG signal intensities are associated with the at least one interface property of the layered structure.

In yet a further aspect, the present invention relates to a method for monitoring fabrication processes of a layered structure having at least one interface. In one embodiment, the method includes the steps of performing non-invasively a SHG measurement on the layered structure in real time, comparing results of the SHG measurement with a target process, where the target process includes a fabrication standard of the layered structure, performing invasively a measurement on the layered structure if at least one departure from the target process is identified by the SHG measurement, and correlating the results of the SHG measurement with the results of the invasive measurement to determine the at least one interface property of the layered structure.

The step of performing a SHG measurement has the step of exposing the layered structure to an incident photon beam to generate SHG signals. The comparing step, in one embodiment, is performed with at least one computer communicating with the SHG measurement and the invasive measurement, respectively.

The invasive measurement includes at least one of an electrical characterization, a contamination measurement, and an interface roughness measurement. The electrical characterization is performed with a pseudo metal-oxide semiconductor field-effect transistor (hereinafter "MOSFET") technique.

In another aspect, the present invention relates to a system for monitoring fabrication processes of a layered structure having at least one interface. In one embodiment, the system has means for performing non-invasively a SHG measurement on the layered structure in real time, means for performing invasively a measurement on the layered structure, and a controller for correlating results of the SHG measurement with results of the invasive measurement to determine the at least one interface property of the layered structure.

In one embodiment, the means for performing non-invasively a SHG measurement has a laser source emitting a beam of pulses that is directed into the layered structure to induce SHG signals.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

Figure 1:
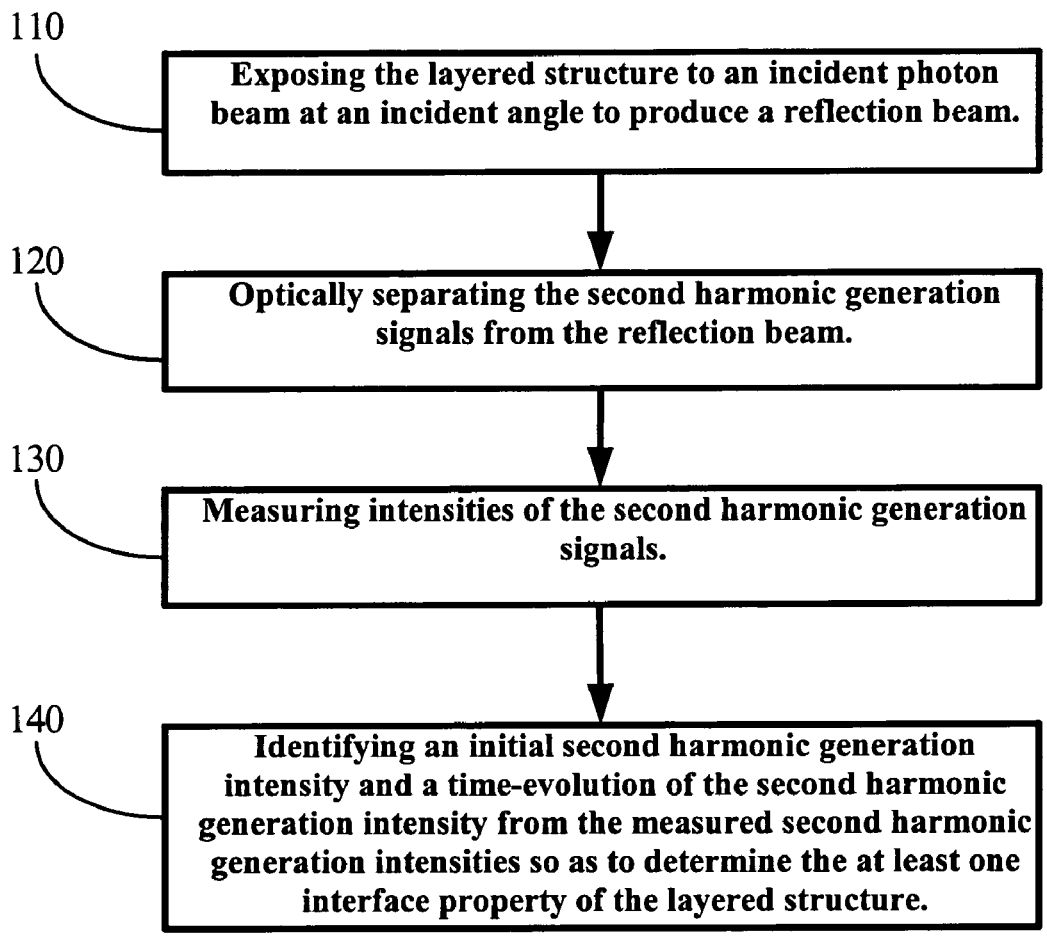
FIG. 1 shows a flowchart for non-invasively optical probing at least one interface property of a layered structure according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which has no influence on the scope of the invention. Additionally, some terms used in this specification are more specifically defined below.

DEFINITIONS

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing various embodiments of the invention and how to practice the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

OVERVIEW OF THE INVENTION

Recent advances in laser technology and nonlinear optics have opened up new venues for fundamental studies of electrical and physical properties of interfaces between various electronic materials in layered structures. Among these approaches, second harmonic generation (hereinafter "SHG") analysis has several advantages. It has been known that the SHG is extremely sensitive to local electric and magnetic fields occurring at surfaces and at interfaces in layered structures. Unlike the electrical characterization methods, the SHG signal detects the electric and magnetic fields at interfaces of layered structures without directly contacting the surfaces of layered structures. Thus, the SHG can be used for in situ measurements. Additionally, the ability of an optical radiation to deeply penetrate into layered structures may make the SHG a powerful probe for electric fields at deeply buried SOI interfaces. These unique features of the SHG have been employed to study long-time carrier dynamics at the silicon-oxide interface [6, 7]. However, applicants believe that there had been no application of the SHG to characterize interface properties in layered structures as disclosed by this disclosure.

This invention in one aspect relates to a method for non-invasively probing at least one interface property of a layered structure. The layered structure at least includes a first layer and a second layer having physics properties substantially different from that of the first layer, where the second layer is deposited on the first layer to form an interface therebetween. The interface can be any type of a semiconductor/dielectric interface, a semiconductor/semiconductor interface, a metal/insulator interface, and a metal/dielectric interface. The interface may be also a metal/metal interface, an insulator/insulator interface or a dielectric/dielectric interface. The at least one interface property of the layered structure includes at least one of interface roughness, interface state density, trapped charge density, surface recombination velocity, electrically active impurity, and interface morphology. Among other things, one unique feature of the present invention is the utilization of SHG signals as a non-invasive optical probe for interface properties of a layered structure. In particular, by measuring the SHG signals induced by interfacial electrical fields that, in turn, are dependent on a number of material parameters in the layered structure, the interface properties of the layered structure can be identified.

Figure 2:
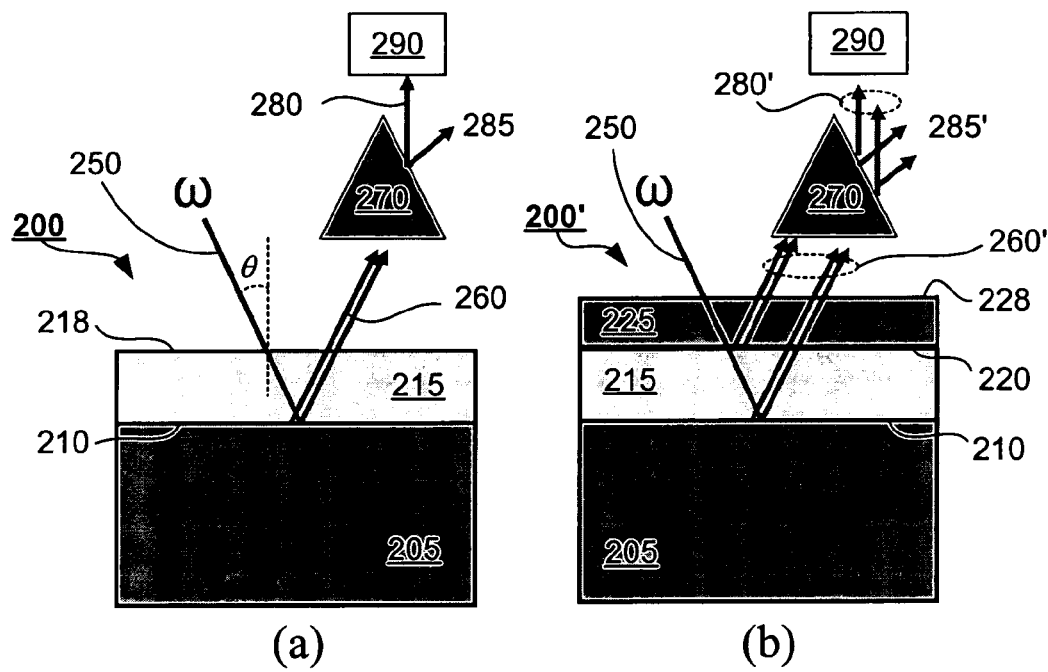
FIG. 2 shows schematically a non-invasively optical probe for at least one interface property of a layered structure according to one embodiment of the present invention corresponding to: (a) the layered structure having one interface, and (b) the layered structure having two interfaces.
Figure 3:
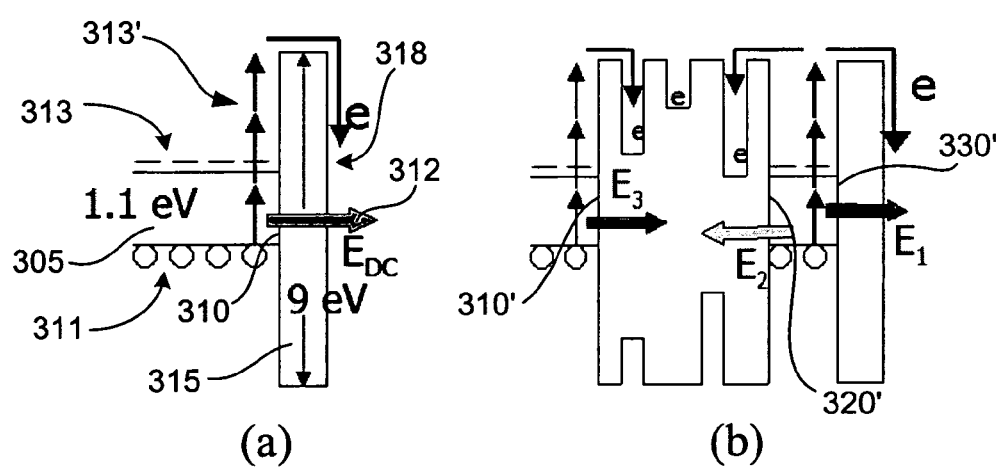
FIG. 3 shows schematically energy band diagrams of a layered structure having photo-induced electron injections according to one embodiment of the present invention corresponding to: (a) a Si/SiO$_2$ layered structure, and (b) a multiple layered structure.

Referring in general now to FIGS. 1–3, and in particular to FIGS. 1 and 2, a method for non-invasively probing at least one interface property of a layered structure, according to one embodiment of the present invention, is schematically illustrated. As shown in FIG. 2a, a layered structure 200 has two layers 205 and 215 and one interface 210 formed therebetween layers 205 and 215. FIG. 2b shows another embodiment where a layered structure 200' has three layers 205, 215 and 225, and two interfaces 210 and 220, with interface 210 formed therebetween layers 205 and 215, and interface 220 formed therebetween layers 215 and 225. The layered structure can be an SOI wafer having two layers (205 and 215) or three layers (205, 215 and 225), with layers 205, 215 and 225 formed with silicon, oxide and silicon, respectively, so that interfaces 210 and 220 are a Si/SiO$_2$ type interface. As shown in FIGS. 1 and 2, at step 110, the layered structure 200 (or 200') is exposed to an incident photon beam 250 at an incident angle, θ, to produce a reflection beam 260 (or 260'). The incident photon beam 250 redistributes carriers across the interface(s) 210 (or 210 and 220) and induces electric fields at the interface, which in turn induce SHG signals in the layered structure 200 (or 200'). The induced SHG signals can be detected from the reflection beam 260 (or 260'). In one embodiment, the incident photon beam 250 includes a monochromatic, pulsed laser beam emitted from a 5 W Verdi pumped Mira Ti:sapphire laser (for example, a Mira 900, Coherent, Inc., Santa Clara, Calif.), at a wavelength of about 800 nm (1.5 eV) with average power of 600–730 mW. Other lasers, such as a free electron laser, can also be employed to practice the current invention.

FIG. 3a shows a schematic energy band diagram and the incident photon induced electron redistribution on a Si/SiO$_2$ interface 310 of an SOI wafer. Band bending is not shown in the diagram. The laser irradiation generates electron-hole pairs 313–311 in the Si region 305, and some of these electrons 313' acquire enough energy from the incident photons to overcome the barrier at the Si/SiO$_2$ interface 310 and are injected into the oxide layer 315. Some of the photo-injected electrons 313' are trapped on free surfaces 318 or at defects (not shown) in the oxide region 315. These trapped electrons are responsible for the time-dependent electric field at the Si/SiO$_2$ interface 310 [6–9], which, in turn, induces SHG signal at the SOI wafer. Hole trapping in the thin oxide layer 315 is less significant since trapped holes easily recombine with de-trapped electrons from the surface 318 [10].

The time-dependent electric field-induced SHG intensity is governed by equation (1) for a single interface. As expressed in equations (1)–(3), E(t) is a quasi-static electric field related to the effective oxide surface charge density, σ(t), which is an integration of oxide volume charge density, ρ(z,t), over the normal axis (z, in this example) to the surface [4–6]:

$$I^{2\omega}(t) = |\chi^{(2)} + \chi^{(3)}E(t)|^2 (I^\omega)^2, \quad (1)$$

-continued $$E(t) = e\sigma(t)/\varepsilon_{St},\quad (2)$$

$$\sigma(t) = \int_0^{T_{Box}} \rho(z,t)dz,\quad (3)$$

where $I^\omega$ and $I^{2\omega}$ are the fundamental and SHG signal intensities, $\chi^{(3)}$, $\chi^{(2)}$ are the third order susceptibility of silicon and the effective SHG susceptibility from other sources, respectively, and $T_{BOX}$ represents a thickness of a corresponding BOX layer.

For a layered structure having multiple interfaces, the total SHG intensity includes contributions from all interfaces. The time-dependent electric field is created independently at each interface. For example, a layered structure shown in FIG. 3b has three interfaces 330', 320' and 310', and accordingly has three electric fields 332' ($E_1$), 322' ($E_2$) and 312' ($E_3$) induced independently at interfaces 330', 320' and 310', respectively. Hence, the detected SHG intensity $I^{2\omega}$ includes the contributions of the electric fields $E_1$, $E_2$ and $E_3$ at the different interfaces, as described by equation (4) given below. The electric field generated at each interface contributes to the total SHG intensity independently, yet it also is affected by an externally applied electric field. The SHG intensity including the contribution of a constant applied field, $E_{Ext}$, can be expressed by equation (5) given below. Depending on the polarity of the external field, it can add to or subtract from the existing interfacial field. Equations (4) and (5) are given below, where the subscript "i" represents the contribution of each interface, $$I^{2\omega}(t) = \sum_i |\chi_i^{(2)} + \chi_i^{(3)}E_i(t)|^2 (I^\omega)^2,\quad (4)$$

$$I^{2\omega}(t) = \sum_i |\chi_i^{(2)} + \chi_i^{(3)}[E_{Ext} + E_i(t)]|^2 (I^\omega)^2.\quad (5)$$

The electric fields in turn are dependent on a number of material parameters that may include interface state densities, trapped charge densities, electrically active impurities, and interface morphology, which affects the effective surface area and thus recombination.

Referring back to FIGS. 1 and 2, at step 120, the SHG signals are optically separated from the reflection beam. In one embodiment, a prism 270 is used for the separation of the SHG signals 280 (280') from the reflection beam 260 (260') due to the wavelength difference between the SHG signals 280 (280') and the fundamental mode 285 (285') of the incident photon beam in the reflection beam 260 (260'). At step 130, intensities of the SHG signals 280 (280') are measured. In one embodiment, a photomultiplier tube 290 (hereinafter "PMT") is employed to detect the SHG signals, which are measured with a photon counter. At step 140, an initial SHG intensity and a time evolution of the SHG intensity are identified from the measured SHG intensities so as to determine the at least one interface property of the layered structure. The initial SHG intensity includes a contribution of the incident photon beam to the SHG signal, which is associated with contributions of $\chi_i^{(2)}$ in equations (1), (4) and (5). The differences between the measured second harmonic generation intensities and the initial second harmonic generation intensity include a contribution of the photo-induced electric field at the Si/SiO$_2$ interfaces to the SHG signals.

Additionally, after the layered structure 200 (or 200') is exposed to the incident photon beam for a certain time, the incident photon beam is blocked off the layered structure for a predetermined period of time. In one embodiment, the blocked-off period of time is about 2 to 3 minutes. This allows the photo-injected election to recombine in the layer structure. For further characterizing the interface properties of the layered structure, a bias electric field may be applied to the layered structure. The bias electric field, in one embodiment, has a DC electric field.

The present invention further relates to a non-invasive optical probe for at least one interface property of a layered structure. The layered structure has at least one interface. In one embodiment, the non-invasive optical probe has a light source for emitting a light beam incident to the layered structure to produce a reflection beam, where the reflection beam comprises a fundamental mode of the incident photon beam and SHG signals. The light source, in one embodiment, includes a 5 W Verdi pumped Mira Ti:sapphire laser, for example, a Mira 900, at a wavelength of about 800 nm (1.5 eV) with average power of 600–730 mW. Other lasers, such as a free electron laser, can also be employed to practice the current invention. The non-invasive optical probe further has optical means for separating SHG signals from the reflection beam. The separated SHG signals can be measured by a detector including a photomultiplier tube and a photon counter.

In another aspect, the invention relates to a non-invasive method for characterizing and monitoring the fabrication processes of a layered structure in a manufacturing/production mode in real-time. The non-invasive optical characterization may replace, or at minimum reduce the need for some of the destructive measurements and improve feedback time. As a process monitor, the SHG application is implemented in the following manner: at first, a non-invasive SHG measurement on the layered structure is performed in real time. At this step, a laser beam is directed to the layered structure to generate SHG signal. The results of the SHG measurement are compared with a target process, where the target process includes a fabrication standard of the layered structure. If at least one departure from the target process is identified by the SHG measurement, an invasive measurement on the layered structure will be performed. Then the results of the SHG measurement are correlated with the results of the invasive measurement to determine the at least one interface property of the layered structure. A computer is employed to communicate with the SHG measurement and the invasive measurement, respectively.

The invasive measurement includes at least one of an electrical characterization, a contamination measurement, and an interface roughness measurement. The electrical characterization is performed with a pseudo-MOSFET technique.

These and other aspects of the present invention are further described below.

METHODS, IMPLEMENTATIONS AND EXAMPLES OF THE INVENTION

Without intend to limit the scope of the invention, further exemplary procedures and preliminary experimental results of the same according to the embodiments of the present invention are given below.

EXAMPLE

Characterization of SOI Wafers

Figure 4:
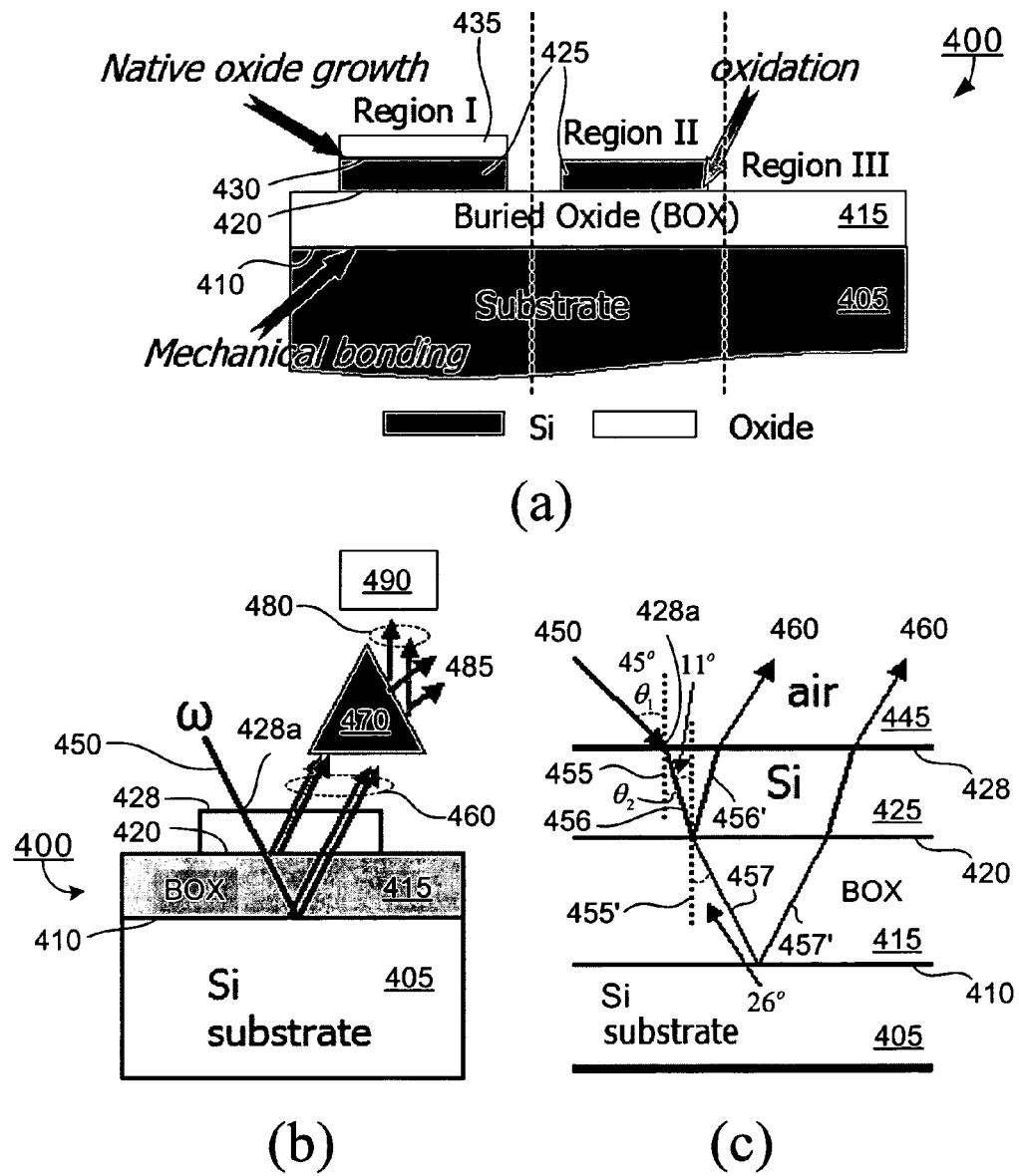
FIG. 4 shows schematically an SOI wafer and a non-invasively optical probe for at least one interface property of the SOI wafer according to one embodiment of the present invention: (a) a cross-sectional view of the SOI wafer, (b) and (c) diagrams of the non-invasively optical probe.

Referring now to FIG. 4, a cross-sectional view of a sample SOI wafer used to practice the present invention is shown. In one embodiment, a UNIBOND™ SOI wafer (SOITEC USA Inc., Peabody, Mass.) is employed to practice the present invention. Other SOI wafers can also be employed to practice the present invention. As shown in FIG. 4a, an SOI wafer 400 has a silicon (hereinafter "Si") substrate 405, a BOX layer 415 bonded on the Si substrate 405 to form a first $Si/SiO_2$ interface 410 therebetween the Si substrate 405 and the BOX layer 415, a Si layer 425 deposited on the BOX layer 415 to form a second $Si/SiO_2$ interface 420 therebetween the BOX layer 415 and the Si layer 425. Additionally, the SOI wafer 400 has an oxide layer 435 natively grown on the Si layer 425 to form a third $Si/SiO_2$ interface 430 therebetween the Si layer 425 and the native oxide layer 435. After the SOI wafer 400 is fabricated, a dry etch technique is used to define Si islands so as to form different layered structures on the SOI wafer 400, which are indicated by Regions I, II and III, respectively, as shown in FIG. 4a. Each of Regions I, II and III contains different layered structures and different $Si/SiO_2$ interfaces. For example, Region III has the Si substrate 405, the BOX layer 415 and the first $Si/SiO_2$ interface 410 formed therebetween. Region II has three layers including the Si substrate 405, the BOX layer 415 and the Si layer 425, and two interfaces including the first $Si/SiO_2$ interface 410 and the second $Si/SiO_2$ interface 420. Region I is a four-layered structure having all of the first $Si/SiO_2$ interface 410, the second $Si/SiO_2$ interface 420 and the third $Si/SiO_2$ interface 430, as described above. The nature of each interface is different. For instance, the first $Si/SiO_2$ interface 410 between the BOX 415 and the Si-substrate 405 is formed by mechanical bonding. The second $Si/SiO_2$ interface 420 between the BOX 415 and the Si layer 425 is created through conventional thermal oxidation. And the native oxide layer 435 is grown on the top of the Si layer 425 by the air ambient to form the third $Si/SiO_2$ interface 430. The native oxide layer 435 can be removed by dipping the sample SOI wafer 400 into a buffered oxide etch solution. In one embodiment, both the Si layer 425 and the Si substrate 405 are p-doped with a doping concentration of $2 \times 10^{15}/cm^3$.

FIG. 4b shows a schematic diagram of a non-invasive SHG probe for Region II of the SOI wafer 400 having the first $Si/SiO_2$ interface 410 and the second $Si/SiO_2$ interface 420. In the embodiment shown in FIG. 4b, an incident photon beam 450 with a wavelength ($\lambda = 2\pi c/\omega$) is directed to a surface 428 of the SOI wafer 400 at an incident point 428a, and transmitted through the Si layer 425 and the BOX layer 415. At each of the first $Si/SiO_2$ interface 410 and the second $Si/SiO_2$ interface 420, the transmitted photon beam is reflected and refracted. The reflected beams by the first $Si/SiO_2$ interface 410 and the second $Si/SiO_2$ interface 420 are transmitted, respectively, toward and through the surface 428 of the SOI wafer 400 to form the reflection beam 460. As described above, the incident photon beam 450 causes carriers in the Si layer 425 and the Si substrate 405 to be redistributed across the first $Si/SiO_2$ interface 410 and the second $Si/SiO_2$ interface 420 and induce the time-dependent electrical fields at the first $Si/SiO_2$ interface 410 and the second $Si/SiO_2$ interface 420, respectively. The induced time-dependent electrical fields, in turn, induce SHG signals in the SOI wafer 400. The induced SHG signals have a wavelength ($\lambda/2$) and are probed by the fundamental mode 485 of the incident photon beam 450. The SHG signals 480 then is separated from the reflection beam 460 by a prism 470 and detected by a PMT 490.

In connection with FIG. 4b, FIG. 4c shows a schematic diagram of the incident photon beam 450 transmitting in the SOI wafer 400 and the reflection beam 460. The incident photon beam 450 in the air 445 is directed to a surface 428 of the SOI wafer 400 at an incident point 428a. An incident angle, $\theta_1$, is defined by the incident photon beam 450 and a normal direction line 455 to the surface 428 of the SOI wafer 400 at the incident point 428a. The incident photon beam 450 at the incident point 428a of the surface 428 of the SOI wafer 400 is split into two beams: a reflected beam (not shown here), and a refracted beam 456 in the Si layer 425. The refracted beam 456 defines a refracted angle, $\theta_2$, relative to the normal 455. The refracted beam 456 travels in the Si layer 425 toward the second $Si/SiO_2$ interface 420 of the SOI wafer 400. At the second interface 420 of the SOI wafer 400, the refracted beam 456 is partially reflected into the Si layer 425 to form a reflected beam 456', and partially refracted into the BOX layer 415 to form a refracted beam 457. The reflected beam 456' travels in the Si layer 425 backward to the surface 428 and then is refracted into the air 445. The refracted beam 457 travels in the BOX layer 415 toward the first $Si/SiO_2$ interface 410. At the first interface 410 of the SOI wafer 400, the refracted beam 457 is partially reflected into the BOX layer 415, indicated by 457'. The reflected beam 457' into the BOX layer 415 is refracted into the Si layer 425, and then refracted into the air 445. The reflected beam of the incident photon beam 450 by the surface 428 at the incident point 280a, and the refracted beam into the air 445 form the reflection beam 460, which carries over induced SHG signals from the first $Si/SiO_2$ interface 410 and the second $Si/SiO_2$ interface 420. The angles of the incident, refracted, and reflected beams at each surface and interface for a fundamental beam are governed by the Snell's law. For example, on the surface 428, the incident angle $\theta_1$ and the refracted angle $\theta_2$ of the fundamental mode of the incident photon beam 450 satisfy that $n_1 \sin \theta_1 = n_2 \sin \theta_2$, where $n_1$ and $n_2$ are a refractive index in the air 445 and in the Si layer 425, respectively. In one embodiment, $\theta_1 = 45°$ and $\theta_2 = 11°$, as shown in FIG. 4c.

In one embodiment, the incident photon beam comprises a laser beam, which can be provided by a 5 W Verdi pumped Mira Ti:sapphire laser (for example, a Mira 900, Coherent, Inc., Santa Clara, Calif.), at a wavelength of about 800 nm (1.5 eV) with average power of 600–730 mW. Other lasers, such as a free electron laser, can also be employed to practice the current invention. As shown in FIG. 4b, after the reflected fundamental signals 485 and SHG signals 480 are separated by a prism 470, the 400 nm wavelength SHG signals 480 are detected by a PMT 490 and measured by a photon counter with a 0.1 s temporal resolution. The area of $1.5 \times 1.5$ mm² between islands allows examination of the first $Si/SiO_2$ interface 410 since the beam diameter of the incident photon beam 450 is approximately about 40 μm. At a beam power of about 730 mW, the average number of generated photons is $2.3 \times 10^{23}$ photons/cm² second.

Table 1 shows material parameters of Si and $SiO_2$ in the SOI wafer 400 shown in FIG. 4 for the wavelengths of 400 nm and 800 nm, respectively. As indicated in Table 1, the penetration depth of a light beam in Si at a wavelength of about 800 nm is about 10 μm, which enables an incident photon beam 450 with a wavelength of about 800 nm to probe buried interfaces 410 and 420 of the SOI wafer 400 having a Si layer 425 with a thickness not greater than 10 μm. On the other hand, the absorption coefficient, K, for SHG signals with a wavelength of about 400 nm becomes significant compared to that of the 800 nm incident photon beam in Si. That is, the penetration depth of the SHG signals is smaller than that of the incident photon beam. The final intensity of a beam can be obtained from the relationship $$I=I_0 \exp(-Kz), \qquad (6)$$

where $I_0$ is the initial intensity, K is the absorption coefficient, defined as $4\pi n_I/\lambda$, and z represents the thickness of the Si layer of the SOI wafer. Note that the SHG intensity generated from the first $Si/SiO_2$ interface 410 is almost unchanged when the SHG signal travels across the BOX layer 415 due to the small absorption coefficient of $SiO_2$. Furthermore, the spatial separation of the SHG signals from both interfaces 410 and 420 is in the range of about 140 nm to 225 nm, depending on the thickness of the BOX layer 415 and the Si layer 405 of the SOI wafer 400. Therefore, the measured SHG signals contain contributions from both the first $Si/SiO_2$ interface 410 and the second $Si/SiO_2$ interface 420.

TABLE 1

Material properties of Si and $SiO_2$ in SOI wafers ($K = 4 \pi n_I/\lambda, 1/K$: penetration depth) for two wavelengths.

| Material | Wavelength $\lambda$ (nm) | Index of Refraction $n_R$ | Extinction Coefficient $n_I$ | Absorption Coefficient K (cm$^{-1}$) |
|---|---|---|---|---|
| Si | 800 | 3.7 | 0.0063 | $10^3$ |
| Si | 400 | 5.49 | 0.356 | $8 \times 10^4$ |
| $SiO_2$ | 800 | 1.45 | — | — |
| $SiO_2$ | 400 | 1.47 | — | $1 \times 10^{-5}$ |

A. SHG Signals from Various Interfaces

Figure 5:
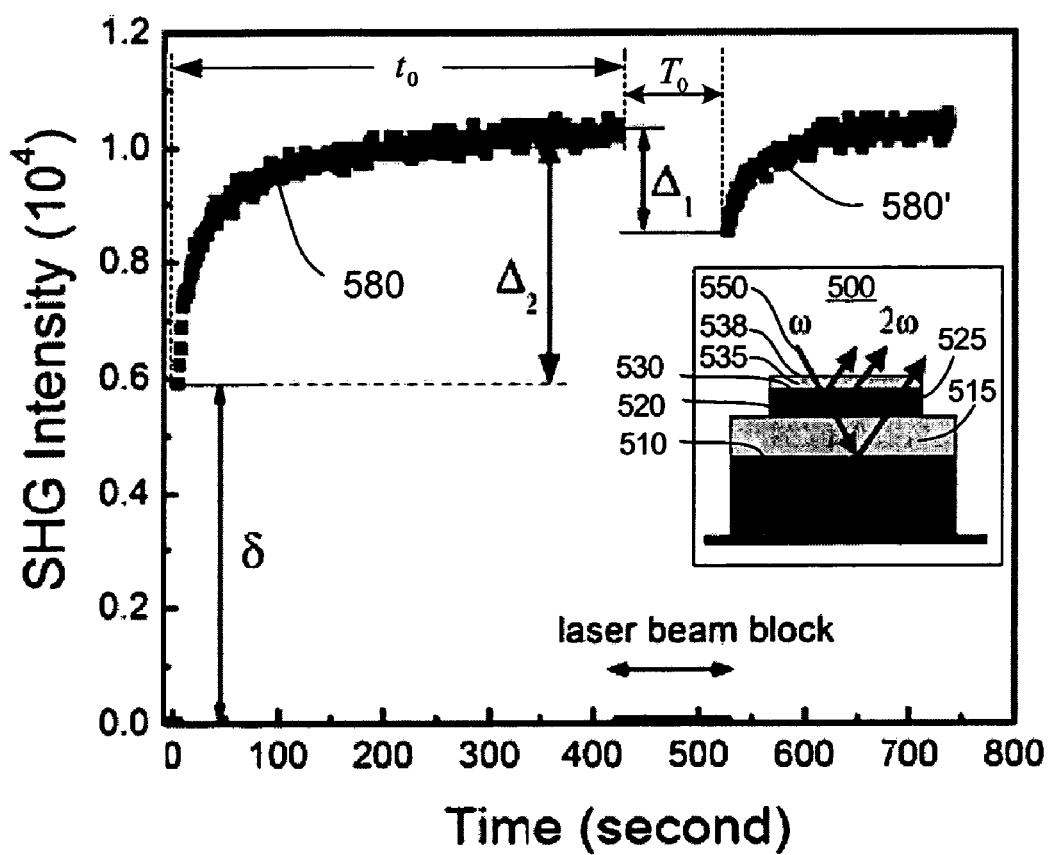
FIG. 5 shows SHG intensities measured from an SOI wafer having three Si/SiO$_2$ interfaces according to one embodiment of the present invention, and a diagram of the SOI wafer (inset).

Referring now to FIG. 5, SHG signal intensity 580 in connection with a UNIBOND™ SOI wafer 500 is shown according to one embodiment of the present invention. The UNIBOND™ SOI wafer 500 corresponds to Region I of the UNIBOND™ SOI wafer shown in FIG. 4a. The Si layer 525 and the BOX layer 515 of the UNIBOND™ SOI wafer 500 have a thickness $T_{Si}$=160 nm and $T_{BOX}$=145 nm, respectively, and the native oxide layer 530 is much thinner than the Si layer 525 and the BOX layer 515. As shown in FIG. 5, when the UNIBOND™ SOI wafer 500 is exposed to an incident photon beam 550, the SHG signal 580 starts with a non-zero intensity, δ, which indicates the contribution of the time-independent term, $\chi^{(2)}$, described in equations (4) and (5). The non-zero initial SHG intensity δ results from the fundamental mode of the incident photon beam 550. As time goes on, the intensity of the SHG signal 580 increases. The SHG signal 580 reaches a saturation valve, indicated by $\Delta_2$, after certain time. The SHG signals detected from the UNIBOND™ SOI wafer 500 are contributed mainly from electrons trapped at the free surface 538 of the native oxide layer 530 [3–5]. The native oxide layers 535 is very thin such that when electrons in the Si layer 525 are photo-injected into the native oxide layers 535, they reach the surface 538 of the native oxide layers 535 and be trapped thereon. As a result, a time-dependent interfacial electric field is generated, and the generated interfacial electric field, in turn, induces the SHG signal. The total SHG intensity 580 in the SOI wafer increases with time. When the time-dependent electric field becomes a constant, the SHG signal 580 reaches a saturation value $\Delta_2$.

As shown in FIG. 5, at time $t_0$ when the SHG signal 580 substantially reaches the saturation value $\Delta_2$, the incident photon beam 550 is blocked off the UNIBOND™ SOI wafer 500 for a period of time, $T_0$, to allow the photo-injected electrons to transport back to the Si layer 525, for example, by tunneling, and recombine therein. In one embodiment, the period of time $T_0$ is about 2 to 3 minutes. When the UNIBOND™ SOI wafer 500 is re-exposed to the incident photon beam 550, the SHG intensity 580' starts with an intensity reduced by $\Delta_1$ from the saturated intensity due to recombination of the trapped electrons on the surface 538 of the native oxide layers 535 when the incident photon beam 550 is blocked. That is, the SHG intensity 580' starts with an intensity of $(\delta+\Delta_2-\Delta_1)$ when the UNIBOND™ SOI wafer 500 is re-exposed at time=$(t_0+T_0)$. The SHG intensity 580' increases with time and reach the saturation value $\Delta_2$ again after certain time.

As shown below, the contributions to the SHG signal 580 from the buried interfaces 510 and 520 of the BOX layer 515 are not significant, compared to the contribution of the thin native oxide layer 535 because of the smaller local field and absorption of the SHG signal in the Si layer 525.

Figure 6:
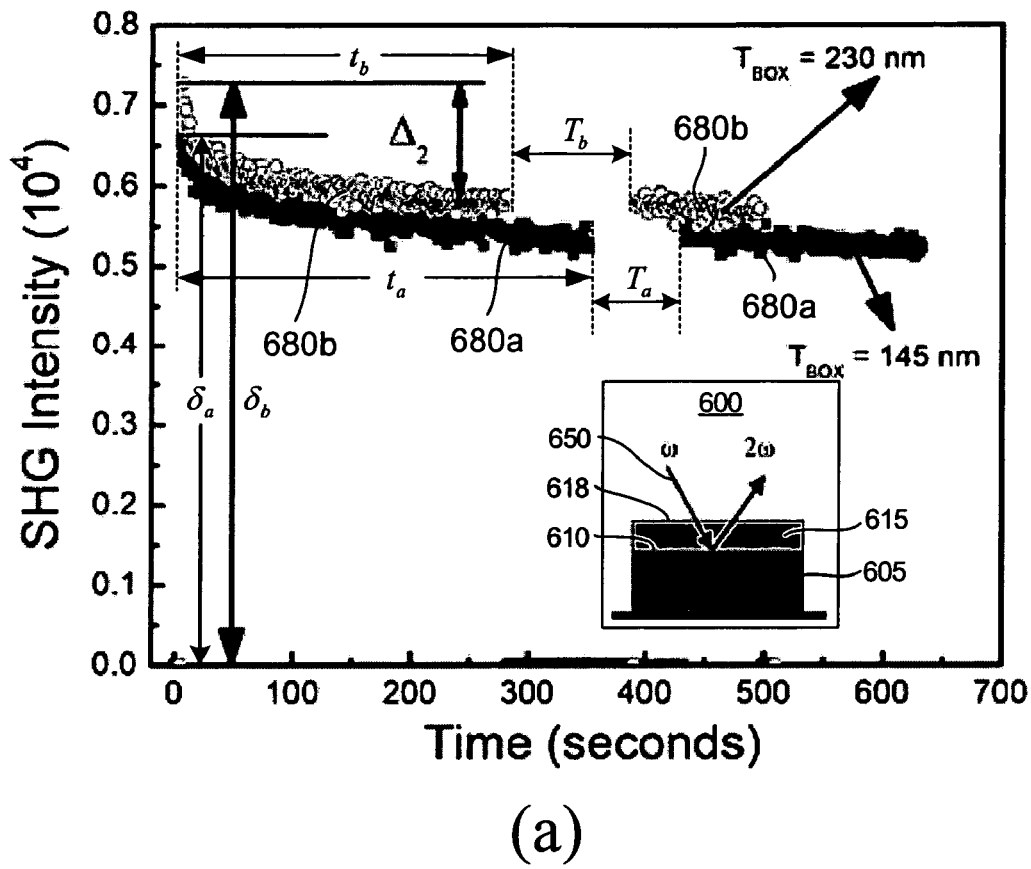
FIG. 6 shows (a) SHG intensities measured from an SOI wafer having one Si/SiO$_2$ interface according to another embodiment of the present invention, and a diagram of the SOI wafer (inset), (b) a schematic energy band diagram of the SOI wafer before being exposed to an incident photon beam, and (c) a schematic energy band diagram of the SOI wafer being exposed to an incident photon beam.
Figure 6:
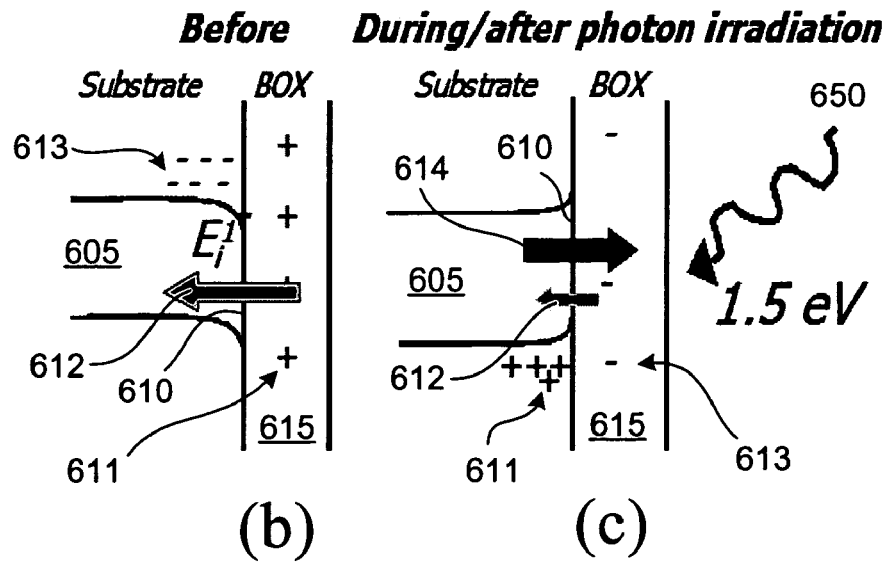

Referring to FIG. 6a, SHG signal intensities 680a and 680b in connection with two UNIBOND™ wafers 600 with BOX thicknesses of about 145 nm and about 230 nm are shown, respectively. The UNIBOND™ wafers 600 each has a configuration corresponding to Region III of the UNIBOND™ wafer shown in FIG. 4a. When the two UNIBOND™ wafers 600, difference only in the BOX thickness, are respectively exposed to an incident photon beam 650 (time=0), the initial SHG intensity $\delta_b$ from the UNIBOND™ wafers 600 with the BOX thicknesses of about 230 nm is larger than the initial SHG intensity $\delta_a$ from the UNIBOND™ wafers 600 with the BOX thicknesses of about 145 nm, due to larger charge separations in the thicker BOX layer (230 nm), compared to the relatively thinner BOX layer (145 nm). Typically, a UNIBOND™ wafer contains residual positive charges in the BOX layer, which makes the flatband voltage negative. As shown in FIG. 6b, the residual positive charges 611 in the BOX layer 615 give rise to the initial electric filed 612, $E_i^1$, at the interface 610, which is in a direction from the BOX layer 615 to the Si substrate 605. When the incident photon beam 650 is incident on the UNIBOND™ wafers 600, it causes electrons 613 to be photo-injected from the Si substrate 605 into the BOX layer 615 so that to generate a time-dependent electric field 614 at the interface 610, directing from the Si substrate 605 to the BOX layer 615, as shown in FIG. 6c. As time increases, the time-dependent electric field starts compensating the initial electric filed 612. The compensation of the initial electric filed 612 is directly reflected in the shape of the SHG signal 680a (680b), that is the SHG signal 680a (680b) decreases from its initial intensity as the UNIBOND™ wafers 600 is being exposed to the incident photon beam 650. In other words, the direction of the electric time-dependent electric field 614 generated by optically induced charge separation is opposite the direction of the initial electric field 612 at the interface 610. When the time-dependent electric field 614 becomes a constant, the SHG signal 680a (680b) is saturated with a constant intensity, indicated by $\Delta_2$ in FIG. 6a. At time=$t_a$ ($t_b$) when the SHG signal 680a (680b) substantially is in the constant intensity $\Delta_2$, the incident photon beam 650 is blocked off the UNIBOND™ SOI wafer 600 for a period of time, $T_a$ ($T_b$), for example, about 2 to 3 minutes. When the UNIBOND™ SOI wafers 600 is re-exposed to the incident photon beam 650 at time=$t_a+T_a$ ($t_b+T_b$), the SHG intensity 680a (680b) is almost same as that at time immediately prior to blocking the incident photon beam 650 off the UNIBOND™ SOI wafer 600.

For a thick oxide layered structure, the photo-injected electrons cannot reach the surface of the thick oxide layer. The time dependence of the SHG signal from the thick oxide interface is caused by charge trapping and de-trapping at interfaces and in the oxide [4]. For a thick oxide, electron-hole recombination during the beam blocking-off periods is smaller than for thin oxides because of the longer time required for charge de-trapping and transport. The time-independent SHG intensity at t=0 for a thick oxide is a simple measure of oxide quality, since it is directly related to the local field created by defects and dangling bonds.

Figure 7:
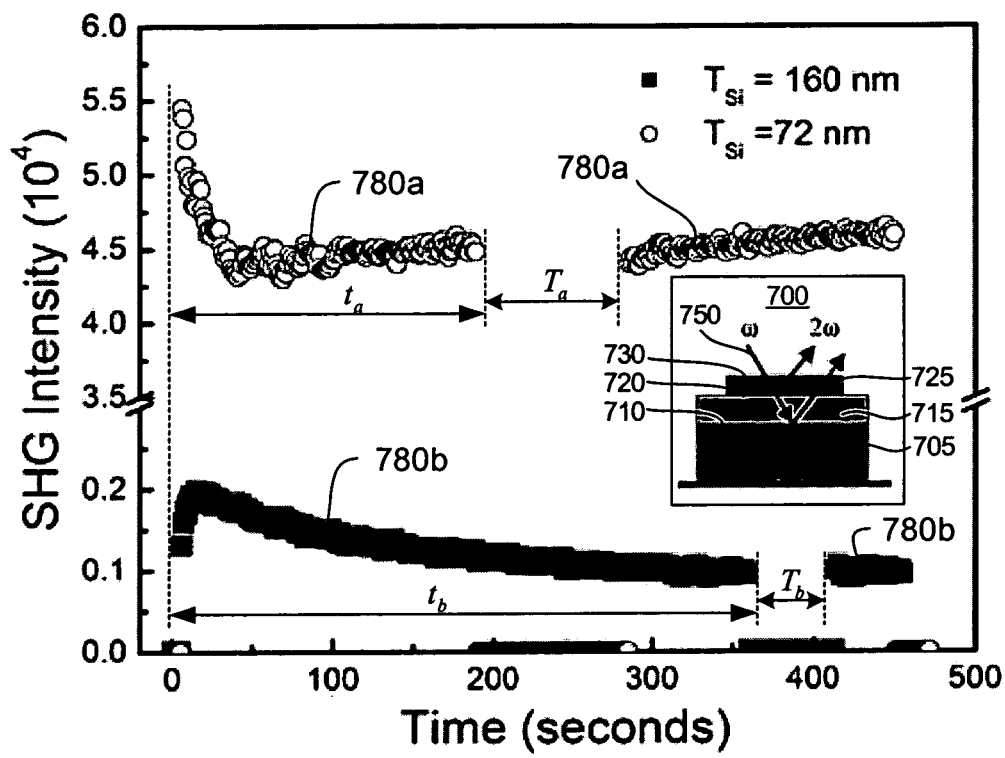
FIG. 7 shows (a) SHG intensities measured from an SOI wafer having two Si/SiO$_2$ interfaces according to an alternative embodiment of the present invention, and a diagram of the SOI wafer (inset), and (b) a schematic energy band diagram of the SOI wafer being exposed to an incident photon beam.
Figure 7:
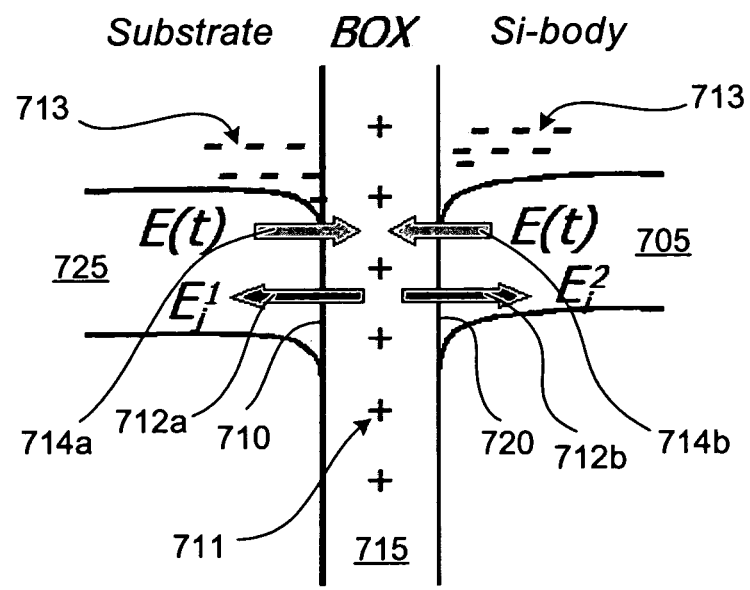

FIG. 7a shows SHG signal intensities 780a and 780b in connection with two UNIBOND™ wafers 700 with different Si body thicknesses. Each of the UNIBOND™ wafers 700 has a Si substrate 705, a BOX layer 715 bonded on the Si substrate 705 to form the first Si/SiO$_2$ interface 710, and a Si body 725 deposited on the BOX layer 715 to form a second Si/SiO$_2$ interface 720. Each of the UNIBOND™ wafers 700 has a configuration corresponding to Region II of the UNIBOND™ wafer shown in FIG. 4a. In one embodiment, the Si body 725 has a thickness of about 72 nm, and the SHG signal from the wafer is indicated by the SHG intensity 780a in FIG. 7a. In another embodiment, the Si body 725 has a thickness of about 160 nm, and the SHG intensity 780b in FIG. 7a represents the SHG signal from the wafer. As shown in FIG. 7, when the two UNIBOND™ wafers 700 are respectively exposed to an incident photon beam 750 (at time=0), the initial SHG intensity $\delta_a$ from the UNIBOND™ wafers 700 with the Si body thicknesses of about 72 nm is larger than the initial SHG intensity $\delta_b$ from the UNIBOND™ wafers 700 with the Si body thicknesses of about 160 nm. The SHG signal 780a from the thinner Si-body wafer (72 nm) is larger the SHG signal 780b from the thicker Si-body wafer (160 nm) due to absorption in the thick Si body. In one embodiment shown in FIG. 7a, only about 27% of the generated SHG intensity at the interface is collected in the detector while the thinner wafer absorbs about 40% of the SHG intensity in the Si body 725. Optical absorption in the BOX layer 715 is negligible. FIG. 7b shows the optically-generated charge separation at both interfaces 710 and 720, which generates time-dependent electric fields 714a and 714b. The time-dependent electric fields 714a and 714b respectively compensate the initial fields 712a, $E_i^1$ and $E_i^2$, induced from the residual positive charges 711 during the wafer process. The optically induced fields at the first interface 710 and the second interface 720 of the SOI wafer are in opposite directions, as shown in FIG. 7b.

B. Applied Bias Effect on SHG Intensity

The SHG signals shown in FIG. 7a contain the electric field induced SHG signals generated at both interfaces 710 and 720. To identify an individual contribution of each interface to the SHG signals, an external electric field is applied across the UNIBOND™ wafer. The externally applied electric field across the BOX layer adds to the optically induced fields at the interfaces due to the charge redistribution.

Figure 8:
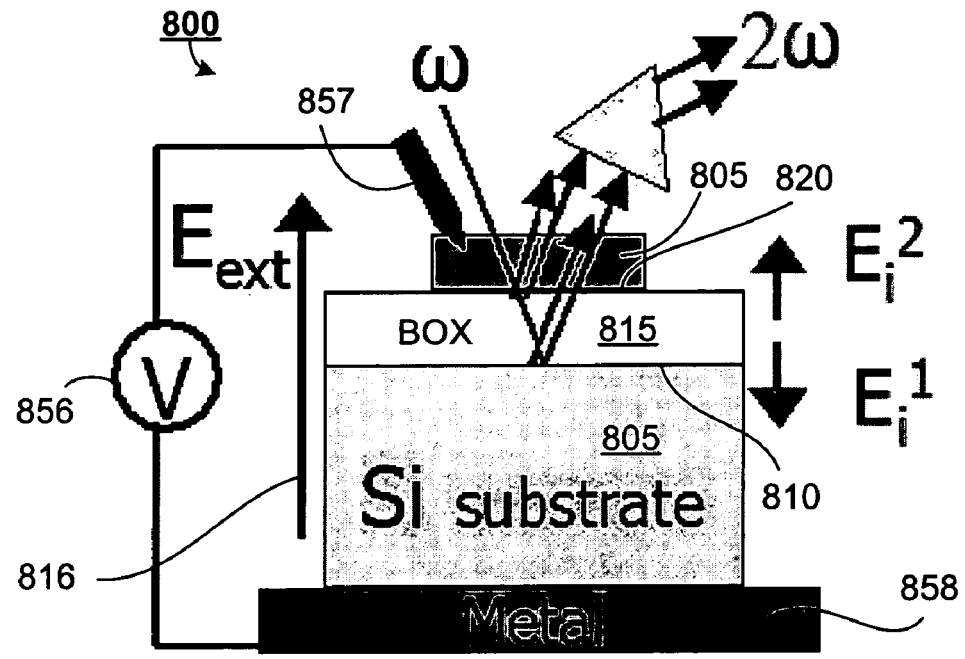
FIG. 8 shows schematically (a) a non-invasively optical probe for at least one interface property of an SOI wafer having a bias electric field applied according to one embodiment of the present invention, (b) a partial energy band diagram of the SOI wafer before being exposed to an incident photon beam and having no bias field applied, (c) a partial energy band diagram of the SOI wafer before being exposed to an incident photon beam and having a bias field applied, and (d) a partial energy band diagram of the SOI wafer being exposed to an incident photon beam and having a bias field applied.
Figure 8:
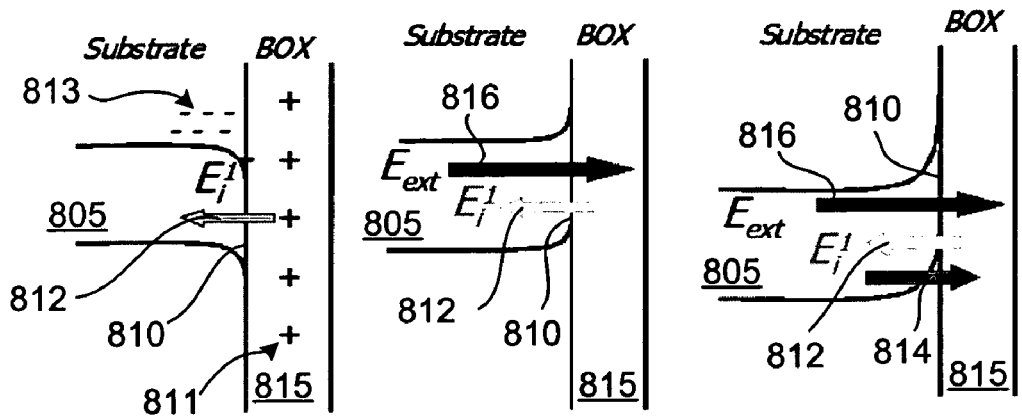

Referring to FIG. 8a, a bias field 816 is applied to a wafer according to one embodiment of the present invention. In this exemplary embodiment shown in FIG. 8a, a wafer 800 has a Si substrate 805, a BOX layer 815 bonded on the Si substrate 805 to form the first Si/SiO$_2$ interface 810, and a Si body 825 deposited on the BOX layer 815 to form a second Si/SiO$_2$ interface 820, corresponding to a configuration of Region II of the wafer shown in FIG. 4a. The bias electric field 816 is generated from a DC electric field generation source 856 having a metal plate 858 as a first output port and an electric probe member 857 as a second output port. The bias electric field 816 is applied to the wafer through coupling the metal plate 858 to Si substrate 805 and the electric probe member 857 to the Si body 825, respectively. In one embodiment, the metal plate 858 is a positive output port of the DC electric field generation source 856 while the probe member 857 is a negative output port of the DC electric field generation source 856 so that the bias electric field 816 applied to the wafer is in a direction from Si substrate 805 to Si body 825.

The charge redistribution at the interface 810 between the Si substrate 805 and the BOX layer 815 due to the external field 816 and photo-induced interfacial electric field 814 are illustrated in FIGS. 8b–8d. FIG. 8b shows an initially interfacial field 812 induced by the residual positive charges 811 in the BOX layer 815, which directs from the BOX layer 815 to the Si substrate 805. The initially interfacial field 812 is compensated by the externally applied field 816, according to the embodiment shown in FIG. 8c. The net interfacial field in the interface 810 increases due to the photon-generated electric field 814, as illustrated in FIG. 8d.

Figure 9:
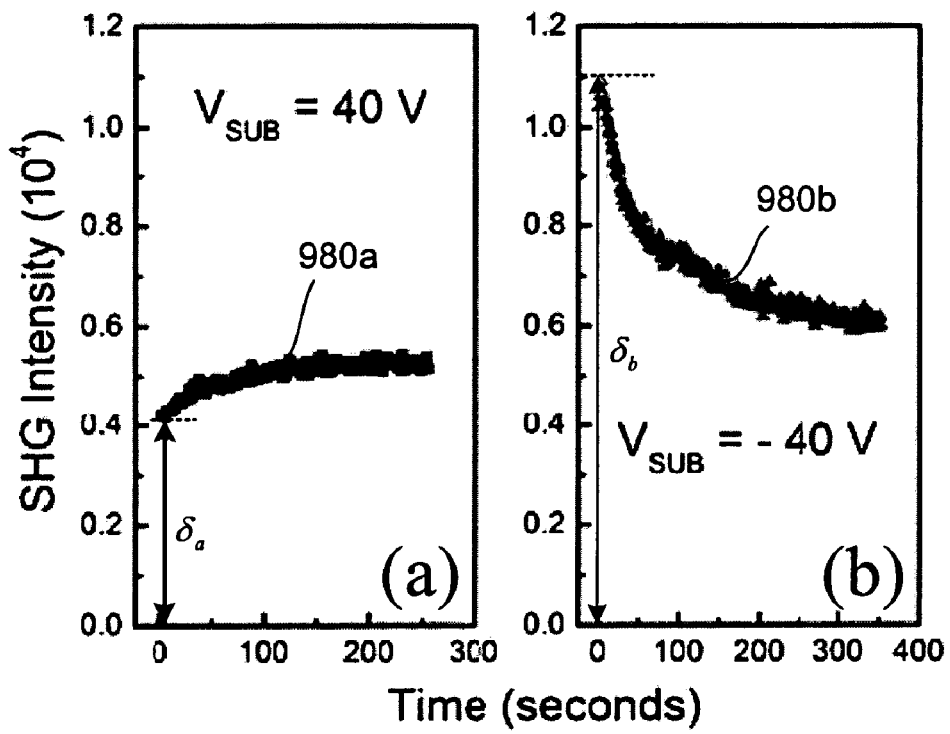
FIG. 9 shows (a) and (b) SHG intensities of an SOI wafer having a bias electric field applied prior to being exposed to an incident photon beam according to an alternative embodiment of the present invention, and (c) and (d) schematic diagrams of the SOI wafer showing photo-induced electric fields at the interfaces and the externally applied bias field.
Figure 9:
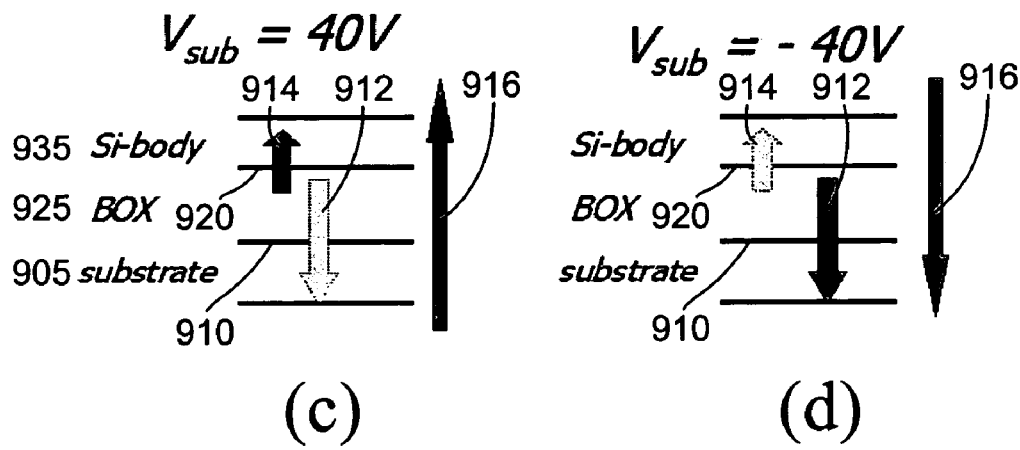

Referring now to FIGS. 9a and 9b, SHG signals in connection with the wafer shown in FIG. 8a with substrate biases of 40 V and −40 V are shown, respectively. In one embodiment, the wafer includes the BOX 915 having a thickness of about 145 nm and the Si body 925 having a thickness of about 160 nm. Compared to the SHG intensities obtained from a wafer without an externally applied bias field shown in FIG. 7a, it is evident that the SHG intensities induced by both time-independent and time-dependent interfacial fields are strongly affected by the externally applied bias fields across the BOX layer. As shown in FIGS. 9a and 9b, the initial SHG intensity $\delta_b$ from the wafer with an external applied bias field $V_{SUB}=-40$ V is more than two times larger than that ($\delta_a$) with $V_{SUB}=40$ V. This implies that the bottom interface 910 creates a larger time-independent electric field 912 than the top interface 920. Considering the different nature of the processes used to form the interfaces 910 and 920 that is, conventional oxidation for the top interface 920 and mechanical bonding for the bottom interface 910, the charge separation is larger at the bottom interface 910 due to more process-related defects, which trap more electrons. When the external bias field 916 is applied across the wafer, it compensates the local fields 912 or 914, depending upon the direction of external bias field 916. FIGS. 9c and 9d shows how the externally applied electric field compensates the interfacial fields. Initially, the interfacial field 914 at the top interface 920 is smaller than the interfacial field 912 at the bottom interface 910, as shown FIGS. 9c. When the external bias field of about 40 V is applied, it compensates the interfacial field 912 at the bottom interface 910, while it adds to the interfacial field 914 at the top interface 920. When the external bias field of about −40 V is applied, it compensates the interfacial field 914 at the top interface 920, while it adds to the interfacial field 912 at the bottom interface 910. The total field at each interface 910 and 920, which is associated with the SHG signal, is modulated when the absolute value of the external bias field is changed.

Figure 10:
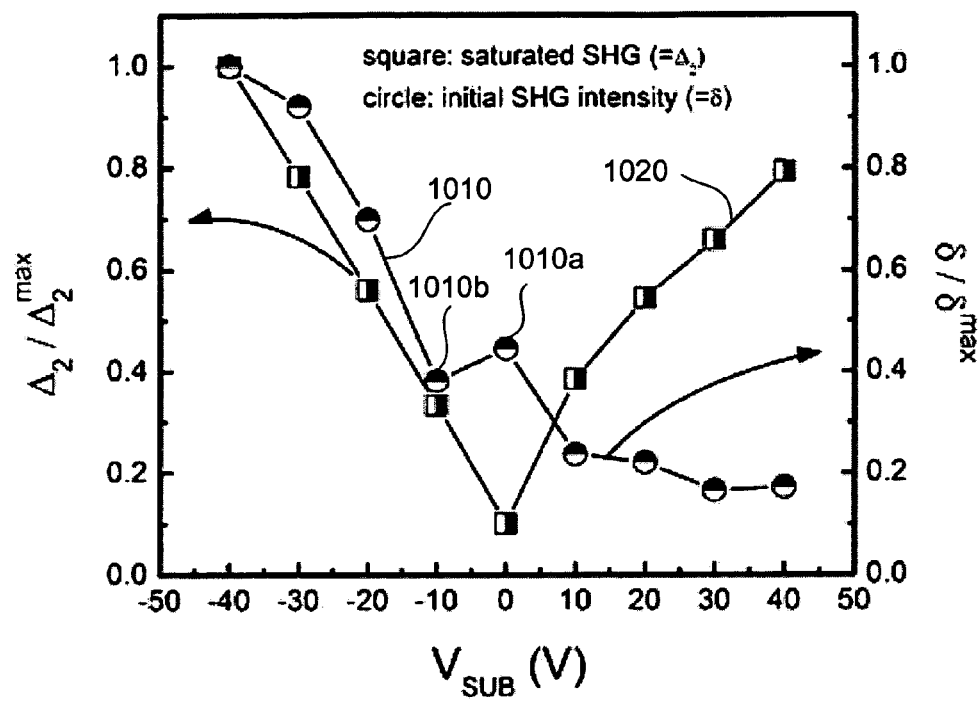
FIG. 10 shows normalized saturated and initial SHG intensities against an externally bias field applied to an SOI wafer according to one embodiment of the present invention.

FIG. 10 shows the normalized initial SHG signals 1010 and the normalized saturated SHG signals 1020 with an externally applied and varying bias field. These SHG signals 1010 and 1020 are acquired from Region II of a UNIBOND™ wafer shown in FIG. 4a, with a Si body thickness $T_{Si}=160$ nm and a BOX layer thickness $T_{BOX}=145$ nm. The initial SHG intensity 1010a for the externally applied bias field of about 0 V is larger than the initial SHG intensity

1010b for the externally applied bias field of about 10 V since the small existing field at the bottom interface is compensated by the external field pointing in the opposite direction.

C. Electrical Characterization via Pseudo-MOSFET Technique

Figure 11:
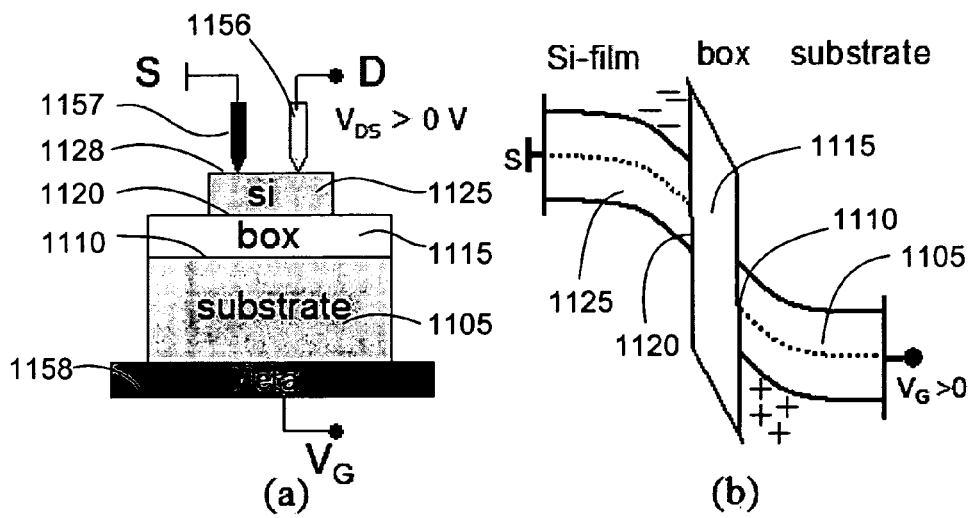
FIG. 11 shows schematic diagrams of (a) electrical characterization via a pseudo-MOSFET technique, and (b) a schematic energy band diagram of the SOI wafer.

In one embodiment, the electrical characterization of an SOI wafer is performed using a 4-point probe and the pseudo-MOSFET (Ψ-MOSFET) technique [3–5]. FIGS. 11a and 11b show schematic diagrams of the pseudo-MOSFET technique applied to the SOI wafer and an energy band diagram of the SOI wafer when applied with a positive bias field, respectively. In this exemplary embodiment shown in FIG. 11, a wafer has a Si substrate 1105, a BOX layer 1115 bonded on the Si substrate 1105 to form the first Si/SiO$_2$ interface 1110, and a Si film 1125 deposited on the BOX layer 1115 to form a second Si/SiO$_2$ interface 1120. The SOI wafer has a configuration corresponding to Region II of the UNIBOND™ SOI wafer shown in FIG. 4a. The pseudo-MOSFET technique includes a source probe member 1157 and a drain probe member 1156 coupled to surface 1128 of the Si film 1125, respectively, and a metal support plate 1158 attached to the Si substrate 1105. In one embodiment, an HP 4156 semiconductor parameter analyzer (Hewlett-Packard Corp., Palo Alto, Calif.) is used to perform a DC characterization of the UNIBOND™ SOI wafer. Other parameter analyzers can also be employed to practice the current invention.

In one embodiment, total dose tests on these sample wafers are performed with 10 keV x-rays at a dose rate of 31 krad(SiO$_2$)/min. The Si substrate of the UNIBOND™ SOI wafer during exposing to incident photons is either DC biased or grounded. Room and high temperature annealing effects after irradiation are characterized in an isochronal manner. The presence of any native oxide on the top of the Si-film creates an extra interface with the Si-film, which is taken into account.

Figure 12:
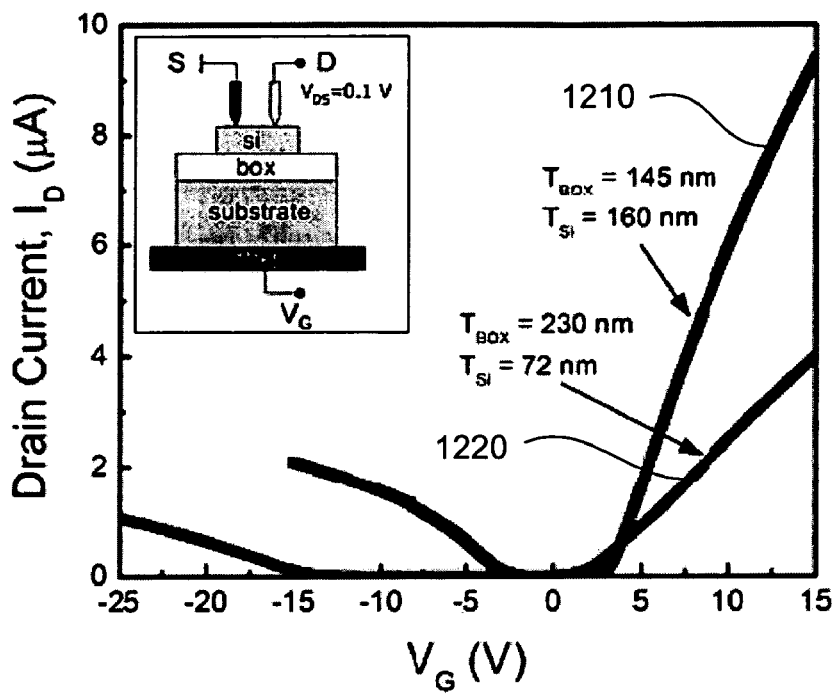
FIG. 12 shows DC $I_D$-$V_{GS}$ characterizations of an SOI wafer having different layer thicknesses by a pseudo-MOSFET technique, and a schematic diagram of the characterizations of the SOI wafer (inset).

Referring to FIG. 12, a current-voltage (I-V) characterization of two UNIBOND™ SOI wafers having different BOX and Si-film thicknesses are shown. Drain current 1210 is measured from a UNIBOND™ SOI wafer having a BOX thickness of about 145 nm and a Si film thickness of about 160 nm, while drain current 1220 is obtained from a UNIBOND™ SOI wafer having a BOX thickness of about 230 nm and a Si film thickness of about 72 nm. The inset figure shows a schematic diagram of the Ψ-MOSFET technique adapted for characterization of the UNIBOND™ SOI wafers. Note that the external bias field dependence of the saturated SHG signals shown in FIG. 10 is analogous to the I-V characterization obtained using the Ψ-MOSFET technique [3–5], as shown in FIG. 12.

Figure 13:
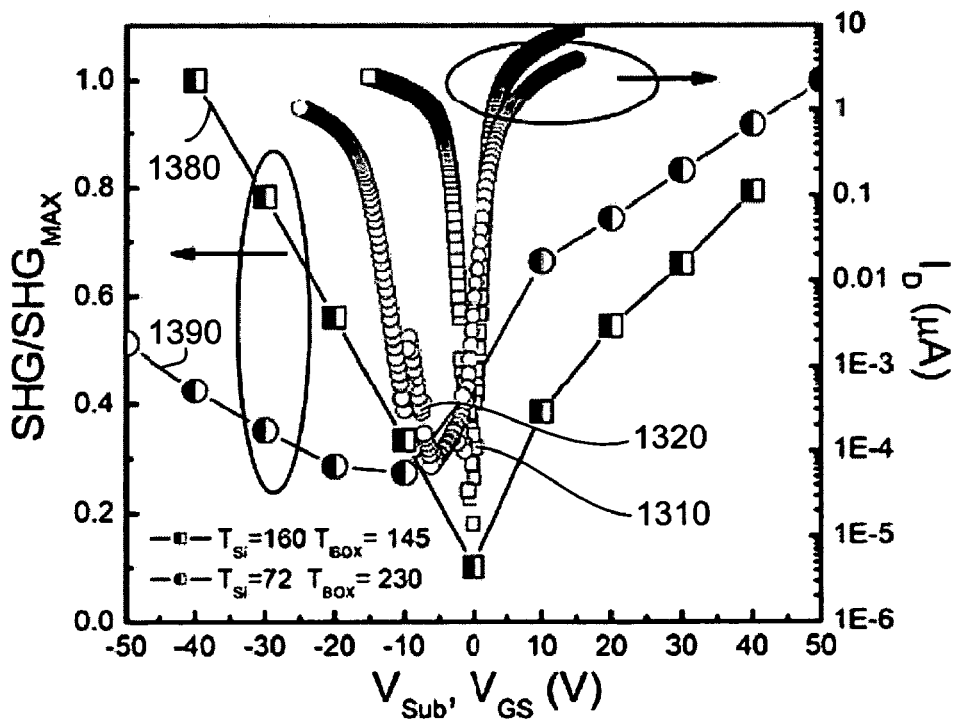
FIG. 13 shows electrical and optical characterizations with varying an externally applied bias field, respectively, according to an alternative embodiment of the present invention.

FIG. 13 shows a direct comparison of a non-invasive optical characterization and an electrical characterization of the UNIBOND™ SOI wafers varying with an external applied bias field, $V_{SUB}$. In one embodiment, two UNIBOND™ SOI wafers are characterized optically and electrically, respectively. One of UNIBOND™ SOI wafers has a BOX thickness of about 145 nm and a Si film thickness of about 160 nm. The non-invasive optical characterization and the electrical characterization are indicated by the optical SHG intensity 1380 and the drain current 1310, respectively. For the UNIBOND™ SOI wafer having a BOX thickness of about 230 nm and a Si film thickness of about 72 nm, the non-invasive optical characterization and the electrical characterization are respectively represented by the optical SHG intensity 1390 and the drain current 1320, as shown in FIG. 13.

The non-zero applied bias field corresponding to the minimum SHG intensity results from the presence of charges at the interfaces and in the oxide. As shown in FIG. 13, for an SOI wafer having a thin Si-film and/or thick BOX layer, for example, $T_{Si}$=72 nm and $T_{BOX}$=230 nm, a minimum of the SHG intensity 1390 is located at a non-zero bias field (about –10 V). The flatband voltages are obtained from a plot of $I_D/(g_m)^{1/2}$ against $V_{sub}$ [13]. The thinner oxide sample has a lower flatband voltage than the thicker oxide sample, which is the x-intercept in the accumulation regime of each curve. The flatband voltages are –1.8 V and –14.2 V for the thinner BOX layer ($T_{BOX}$=145 nm) and the thicker BOX layer ($T_{BOX}$=230 nm), respectively. Since the field is smallest near flatband, the SHG minimum should occur near flatband.

D. Total Dose and Annealing Effects on SHG Signals

Figure 14:
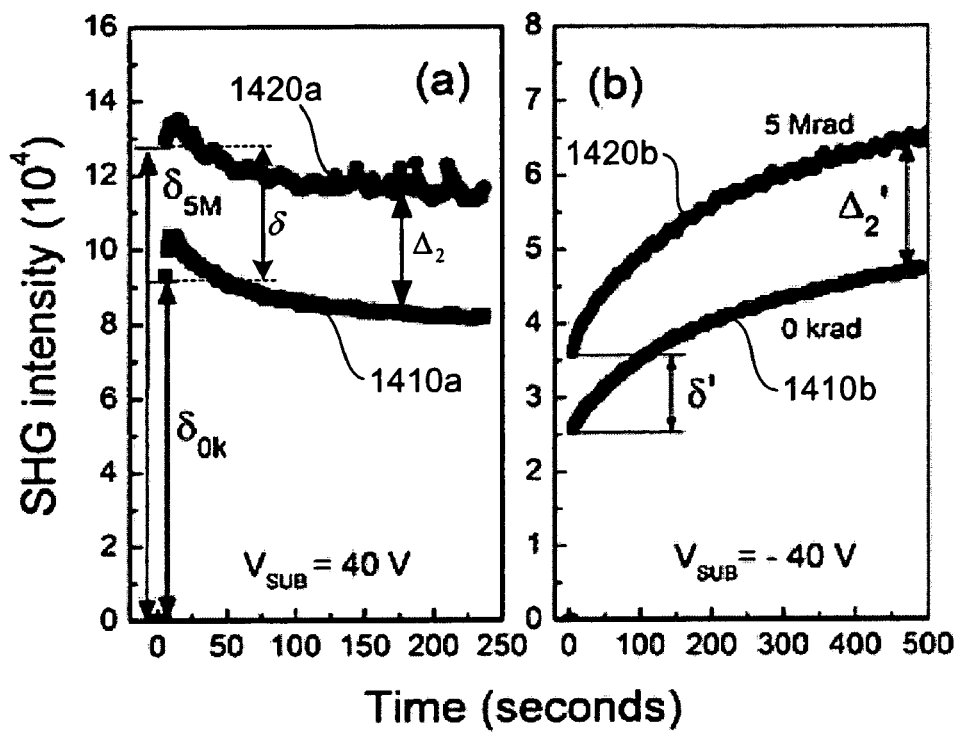
FIG. 14 shows SHG intensities of an SOI wafer before and after a total dose of 5 Mrad against an externally applied bias field according to an alternative embodiment of the present invention.

Radiation-induced charges can change the charge distribution in the Si body of an SOI wafer, which directly affects the local fields at the interfaces [11, 12]. Referring to FIG. 14, the SHG signals 1410a, 1420a, 1410b and 1420b from a UNIBOND™ SOI wafer having a Si body thickness of about 72 nm and an BOX thickness of about 230 nm with a total dose of about 5 Mrad(SiO$_2$) are shown according to one embodiment of the present invention. The UNIBOND™ SOI wafer is exposed to an incident photon beam with a power of about 600 mW, and has an external bias field of about 40 V and –40 V applied, respectively. Both the initial and saturation levels of the SHG intensities increase with the dose of about 5 Mrad(SiO$_2$), regardless of the applied bias field. For example, for an external bias field of 40 V, the initial and saturation levels of the SHG intensities increase by δ and $\Delta_2$ from zero dose to a dose of about 5 Mrad(SiO$_2$), respectively. For an external bias field of –40 V, the initial and saturation levels of the SHG intensities increase by δ' and $\Delta'_2$ from zero dose to a dose of about 5 Mrad(SiO$_2$), respectively, as shown in FIG. 14. This indicates that radiation-induced trapped charges increase the local fields at the interfaces of the UNIBOND™ SOI wafer.

Figure 15:
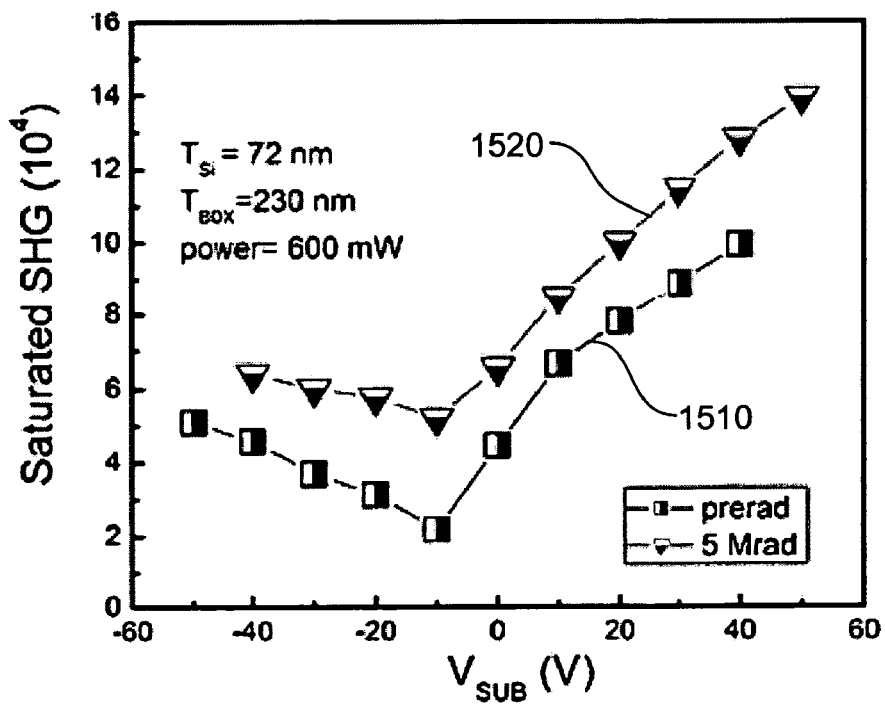
FIG. 15 shows saturated SHG intensities of an SOI wafer before and after a total dose of 5 Mrad against an externally applied bias field according to an alternative embodiment of the present invention.

In one embodiment, effects of an externally applied bias field on the saturated SHG signal from an irradiated UNIBOND™ SOI wafer are examined. The absolute SHG magnitude increases with a dose of radiation. FIG. 15 shows the SHG signal 1510 generated from the UNIBOND™ SOI wafer before a total dose of 5 Mrad, and the SHG signal 1520 generated from the UNIBOND™ SOI wafer after a total dose of 5 Mrad, against the external bias field, respectively. The SHG signal intensity 1520 is greater than the SHG signal intensity 1510 over variety values of the externally applied bias field, as shown in FIG. 15, where the UNIBOND™ SOI wafer has $T_{Si}$=72 nm and $T_{BOX}$=230 nm, and the incident photon beam has a power of about 600 mW.

Figure 16:
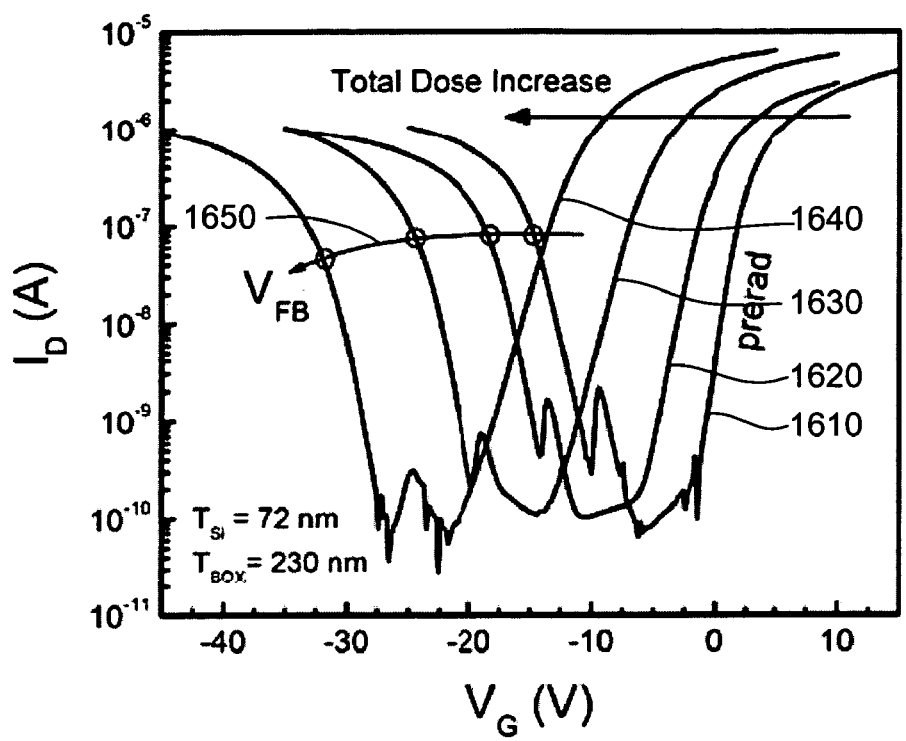
FIG. 16 shows I-V characterization of an SOI wafer with increasing total dose.

The shift in the intensities of the SHG signals after irradiation is analogous to the shift observed in the I-V characterization obtained from the pseudo-MOSFET technique. Referring to FIG. 16, the I-V characterization in connection with a UNIBOND™ SOI wafer with $T_{Si}$=72.1 nm and $T_{BOX}$=230 nm with increasing total dose is shown. In FIG. 16, currents 1610, 1620, 1630 and 1640 are respectively corresponding to results of the I-V characterization of the UNIBOND™ SOI wafer with a dose of from zero to non-zero, in a manner of increasing dose. The flatband voltage shift 1650 is due to radiation induced oxide charges, which also cause an increase in the SHG intensity, as shown in FIG. 15. These changes in the SHG signals can be used to obtain information about the oxide trap charges for SOI wafers subjected to ionizing radiation.

Figure 17:
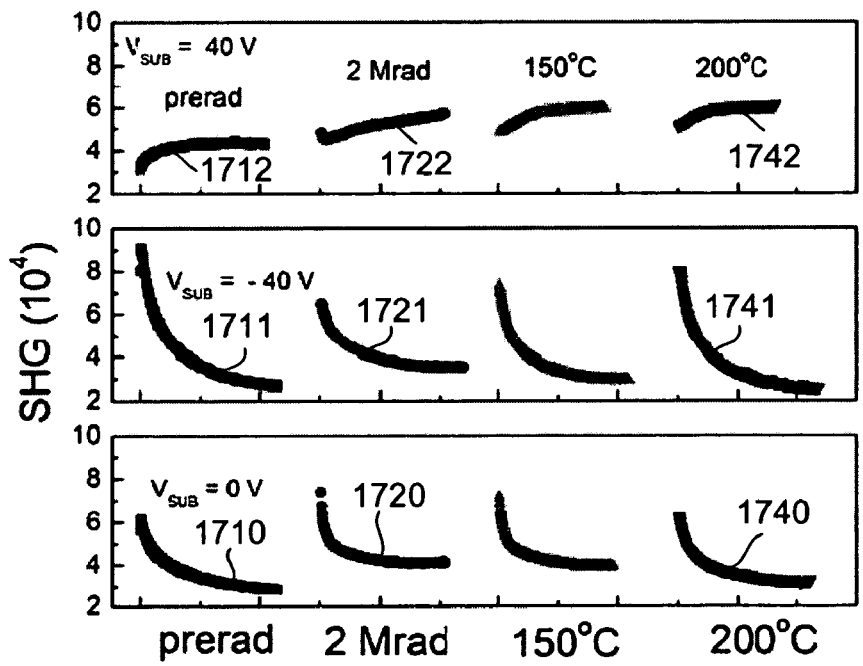
FIG. 17 shows SHG intensities of an SOI wafer with different doses and annealed at selected temperatures, respectively, according to an alternative embodiment of the present invention.

FIG. 17 shows the SHG signals collected from Region II of a UNIBOND™ SOI wafer shown in FIG. 4a with a Si thicknesses of about 125 nm and an oxide thicknesses of about 143 nm. The UNIBOND™ SOI wafer is irradiated at a dose rate of about 31 krad($SiO_2$)/min with the top and bottom of the wafer shorted during irradiation. Isochronal annealing is performed after a total dose of 2 Mrad ($SiO_2$), for 10 minutes at selected temperatures. As shown in FIG. 17, SHG intensities 1710, 1711 and 1722 are generated from a zero dose UNIBOND™ SOI wafer with an external applied bias field of about 0 V, −40 V and 40 V, respectively. The initial and saturation levels of the SHG intensities 1720, 1721 and 1722 measured from the UNIBOND™ SOI wafer after a dose of 2 Mrad($SiO_2$) are changed with the external applied bias field of about 0 V, −40 V and 40 V, respectively. For annealing of the UNIBOND™ SOI wafer after a dose of 2 Mrad($SiO_2$) at 200° C., the both initial and saturation level of the SHG intensities 1740 and 1741 with the external applied bias field of about 0 V, −40 V are fully recovered to its level before a dose of 2 Mrad($SiO_2$), while that for $V_{SUB}$=40 V has still not recovered. The different temperature responses of the interfaces indicate different annealing rates.

In the present invention, among other things, charge generation, transport, and recombination processes in SOI wafers are probed by using a non-invasive optical SHG technique. The electric fields at the interfaces vary with time due to electron trapping. The presence of a thin native oxide layer on the top Si film contributes significantly to the SHG intensity due to the strong time-dependent electric field generated by electrons transported to the surface. For the thick buried oxide, the electric field is primarily due to carrier trapping at the interface, and it varies with time weakly. The SHG signals depend strongly on the externally applied electric field, which can differentiate the contribution of each interface to the total SHG signal. These unique features of SHG signals generated from a layered structure can be used to characterize and monitor fabrication process of the layered structure in a manufacturing/production mode in real-time. Implementation of the methodology can leverage existing tool platform infrastructure including wafer handling, computers, etc.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1]. S. Cristoloveanu and S. S. Li, "Electrical characterization of SOI materials and devices," Norwell, Mass.: Kluwer Academic, Dordrecht, 1995.

[2]. B. J. Mrstik, H. L. Hughes, P. J. McMarr, R. K. Lawrence, D. I. Ma, I. P. Isaacson, and R. A. Walker, "Hole and electron trapping in ion implanted thermal oxides and SIMOX," *IEEE Trans. Nucl. Sci.*, vol. 47, pp. 2189–2195, December 2000.

[3]. S. Cristoloveanu, D. Munteanu, and M. S. T. Liu, "A review of the pseudo-MOS transistor in SOI wafers: operation, parameter extraction, and applications," *IEEE Trans. Electron Dev.*, vol. 47, No. 5, pp. 1018–1027, 2000.

[4]. S. Cristoloveanu and Stephen Williams, "Point-contact pseudo-MOSFET in-situ characterization of as-grown silicon-on-insulator wafers," *IEEE Electron Dev. Lett.*, vol. 13, No. 2, pp. 102–104, 1992.

[5]. B. Jun, X. Zhou, E. J. Montes, R. D. Schrimpf, D. M. Fleetwood, and S. Cristoloveanu, "Charge separation techniques for irradiated pseudo-MOS SOI transistors", *IEEE Trans. Nucl. Sci.* vol. 50. pp. 1891–1895, December 2003.

[6]. J. F McGilp, "A review of optical second-harmonic and sum-frequency generation at surfaces and interfaces," *J. Phys. D: Appl. Phys.* vol. 29, p. 1812, 1996.

[7]. G. Lüpke, "Characterization of semiconductor interfaces by second-harmonic generation," *Surf. Sci. Rep.*, vol. 35, p. 75, 1999.

[8]. J. G. Mihaychuk, J. Bloch, and H. M. van Driel, "Time-dependent second-harmonic generation from the Si—$SiO_2$ interface induced by charge transfer," *Opt Lett.* vol. 20, pp. 2063–2065, 1995.

[9]. J. Bloch, J. G. Mihaychuk, and H. M. van Driel, "Electron photoinjection from silicon to ultrathin $SiO_2$ films via ambient oxygen," *Physical Review Letters*, vol. 77, pp 920–923, 1996.

[10]. W. Wang, G. Lüpke, M. Di Ventra, S. T. Pantelides, J. M. Gillian, and N. H. Tolk, "Coupled electron-hole dynamics at the Si/$SiO_2$ interface," *Phys. Rev. Lett.* vol. 81, no. 19, pp. 4224–4227, November 1998.

[11]. R. Pasternak, Y. V. Shirokaya, Z. Marka, J. K. Miller, S. N. Rashkeev, S. T. Pantelides, N. H. Tolk, B. K. Choi, R. D. Schrimpf, and D. M. Fleetwood, "Laser detection of radiation enhanced electron transport in ultra-Thin oxides," *Nuclear Instruments and Methods in Physics Research Sec. A.* vol. 514, pp. 150–155, 2003.

[12]. Z. Marka, S. K. Singh, W. Wang, S. C. Lee, J. Kavich, B. Glebov, S. N. Rashkeev, A. P. Karmarkar, R. G. Albridge, S. T. Pantelides, R. D. Schrimpf, D. M. Fleetwood, and N. H. Tolk, "Characterization of X-ray radiation damage in Si/$SiO_2$ structures using second-harmonic generation," *IEEE Trans. Nucl. Sci.* vol. 47, No. 6, pp. 2256–2261, December 2000.

[13]. G Ghibaudo "New method for the extraction of MOSFET parameters," *Electronics Lett.*, vol. 24, p. 543–544, 1988.

What is claimed is:

1. A method for non-invasively probing at least one interface property of a layered structure, wherein the layered structure at least includes a silicon substrate and an oxide layer deposited on the silicon substrate to form a first Si/$SiO_2$ interface therebetween, comprising the steps of:

a. exposing the layered structure to an incident photon beam at an incident angle to produce a reflection beam, wherein the incident photon beam redistributes carriers across the first Si/$SiO_2$ interface and induces an electric field at the first Si/$SiO_2$ interface, and the reflection beam comprises a fundamental mode of the incident photon beam and second harmonic generation signals;

b. optically separating the second harmonic generation signals from the reflection beam;

c. measuring intensities of the second harmonic generation signals; and d. identifying an initial second harmonic generation intensity and a time-evolution of the second harmonic generation intensity from the measured second harmonic generation intensities so as to determine the at least one interface property of the layered structure, wherein the initial second harmonic generation intensity includes a contribution of the incident photon beam to the second harmonic generation, and differences between the measured second harmonic generation intensities and the initial second harmonic generation intensity includes a contribution of the induced electric field at the first $Si/SiO_2$ interface to the second harmonic generation.

2. The method of claim 1, further comprising the step of blocking the incident photon beam off the layered structure at a predetermined time for a predetermined period of time.

3. The method of claim 2, wherein the layered structure further comprises a silicon layer deposited on the oxide layer to form a second $Si/SiO_2$ interface therebetween.

4. The method of claim 3, further comprising the step of applying a bias electric field to the layered structure.

5. The method of claim 4, wherein the bias electric field comprises a DC electric field.

6. The method of claim 1, wherein the incident photon beam comprises substantially monochromatic electromagnetic radiation.

7. The method of claim 6, wherein the substantially monochromatic electromagnetic radiation comprises a laser beam.

8. The method of claim 7, wherein the laser beam comprises a pulsed laser beam.

9. The method of claim 1, wherein the optically separating step is performed with a prism.

10. The method of claim 1, wherein the measuring step comprises the step of detecting the second harmonic generation signals by a photomultiplier tube.

11. The method of claim 10, wherein the measuring step is performed with a photon counter.

12. The method of claim 1, wherein the at least one interface property of the layered structure comprises at least one of interface roughness, interface state density, trapped charge density, surface recombination velocity, electrically active impurity, and interface morphology.

13. A method for non-invasively probing at least one interface property of a layered structure, wherein the layered structure at least includes a first layer and a second layer having physics properties substantially different from that of the first layer, the second layer deposited on the first layer to form an interface therebetween, comprising the steps of:

a. exposing the layered structure to an incident photon beam at an incident angle to produce a reflection beam, wherein the incident photon beam redistributes carriers across the interface and induces an electric field at the interface, and the reflection beam comprises a fundamental mode of the incident photon beam and second harmonic generation signals;

b. measuring intensities of the second harmonic generation signals from the reflection beam; and c. identifying an initial second harmonic generation intensity and a time evolution of the second harmonic generation intensity from the measured second harmonic generation intensities so as to determine the at least one interface property of the layered structure, wherein the initial second harmonic generation intensity includes a contribution of the incident photon beam to the second harmonic generation, and differences between the measured second harmonic generation intensity and the initial second harmonic generation intensity include a contribution of the induced electric field at the interface to the second harmonic generation.

14. The method of claim 13, further comprising the step of blocking the incident photon beam off the layered structure at a predetermined time for a predetermined period of time.

15. The method of claim 14, further comprising the step of applying a bias electric field to the layered structure.

16. The method of claim 15, wherein the bias electric field comprises a DC electric field.

17. The method of claim 13, where the interface comprises one of a semiconductor/dielectric interface, a semiconductor/semiconductor interface, a metal/insulator interface, and a metal/dielectric interface.

18. The method of claim 13, wherein the incident photon beam comprises substantially monochromatic electromagnetic radiation.

19. The method of claim 18, wherein the substantially monochromatic electromagnetic radiation comprises a laser beam.

20. The method of claim 19, wherein the laser beam comprises a pulsed laser beam.

21. The method of claim 13, wherein the measuring step comprises the step of detecting the second harmonic generation signals by a photomultiplier tube.

22. The method of claim 21, wherein the measuring step is performed with a photon counter.

23. The method of claim 13, wherein the at least one interface property of the layered structure comprises at least one of interface roughness, interface state density, trapped charge density, surface recombination velocity, electrically active impurity, and interface morphology.

24. A non-invasive optical probe for at least one interface property of a layered structure, wherein the layered structure at least includes a first layer and a second layer having physics properties substantially different from that of the first layer, the second layer deposited on the first layer to form an interface therebetween, comprising:

a. a light source for emitting a light beam incident to the layered structure to produce a reflection beam, wherein the reflection beam comprises a fundamental mode of the incident photon beam and second harmonic generation signals;

b. optical means for separating second harmonic generation signals from the reflection beam; and c. a detector for measuring intensities of the second harmonic generation signals, wherein the measured second harmonic generation signal intensities are associated with the at least one interface property of the layered structure.

25. The non-invasive optical probe of claim 24, further comprising a source of an electric field for generating a bias field applied to the layered structure.

26. The non-invasive optical probe of claim 24, wherein the light source comprise a laser.

27. The non-invasive optical probe of claim 24, where the interface comprises one of a semiconductor/dielectric interface, a semiconductor/semiconductor interface, a metal/insulator interface, and a metal/dielectric interface.

28. The non-invasive optical probe of claim 24, wherein the first layer of the layered structure comprises silicon.

29. The non-invasive optical probe of claim 28, wherein the second layer of the layered structure comprises oxide.

30. The non-invasive optical probe of claim 29, wherein the layered structure further comprises a silicon layer deposited on the second layer of the layered structure.

31. The non-invasive optical probe of claim 24, wherein the detector comprises a photomultiplier tube.

32. A non-invasive optical probe for at least one interface property of a layered structure having at least one interface, comprising:
   a. a laser source emitting a beam of pulses, the beam of pulses being directed into the layered structure so as to induce second harmonic generation signals; and
   b. an optical system for measuring intensities of the induced second harmonic generation signals,
wherein the measured second harmonic generation signal intensities are associated with the at least one interface property of the layered structure.

33. The non-invasive optical probe of claim 32, wherein the at least one interface comprises one of a semiconductor/dielectric interface, a semiconductor/semiconductor interface, a metal/insulator interface, and a metal/dielectric interface.

34. A method for monitoring fabrication processes of a layered structure having at least one interface, comprising the steps of:
   a. performing non-invasively a second harmonic generation measurement on the layered structure in real time;
   b. comparing results of the second harmonic generation measurement with a target process, wherein the target process comprises a fabrication standard of the layered structure;
   c. performing invasively a measurement on the layered structure if at least one departure from the target process is identified by the second harmonic generation measurement; and
   d. correlating the results of the second harmonic generation measurement with the results of the invasive measurement to determine the at least one interface property of the layered structure.

35. The method of claim 34, wherein the step of performing a second harmonic generation measurement comprises the step of exposing the layered structure to an incident photon beam to generate second harmonic generation signals.

36. The method of claim 34, wherein the comparing step is performed with at least one computer communicating with the second harmonic generation measurement and the invasive measurement, respectively.

37. The method of claim 34, wherein the invasive measurement comprises at least one of an electrical characterization, a contamination measurement, and an interface roughness measurement.

38. The method of claim 37, wherein the electrical characterization is performed with a pseudo metal-oxide semiconductor field-effect transistor technique.

39. A system for monitoring fabrication processes of a layered structure having at least one interface, comprising:
   a. means for performing non-invasively a second harmonic generation measurement on the layered structure in real time;
   b. means for performing invasively a measurement on the layered structure; and
   c. a controller for correlating results of the second harmonic generation measurement with results of the invasive measurement to determine the at least one interface property of the layered structure.

40. The system of claim 39, wherein the means for performing non-invasively a second harmonic generation measurement comprises a laser source emitting a beam of pulses directed into the layered structure to induce second harmonic generation signals.

41. The system of claim 39, wherein the invasive measurement comprises at least one of an electrical characterization, a contamination measurement, and an interface roughness measurement.

42. The system of claim 41, wherein the electrical characterization is performed with a pseudo metal-oxide semiconductor field-effect transistor technique.

* * * * *

UNITED STATES PATENT AND TRADEMARK OFFICE
CERTIFICATE OF CORRECTION

| | | |
|---|---|---|
| PATENT NO. | : 7,158,284 B2 | Page 1 of 1 |
| APPLICATION NO. | : 11/019906 | |
| DATED | : January 2, 2007 | |
| INVENTOR(S) | : Michael Lee Alles et al. | |

It is certified that error appears in the above-identified patent and that said Letters Patent is hereby corrected as shown below:

Column 1 and Column 2:

Column 1, Lines 65-67 through Column 2, Lines 1-2: "The present invention was made with Government support under a contract F49620-99-1-0289 awarded by Air Force Office of Scientific Research, and by Office of Naval Research. The United States Government may have certain rights to this invention pursuant to these grants." should read --The present invention was made with Government support under a contract No. F49620-99-1-0289 awarded by Air Force Office of Scientific Research, and contract Nos. N00014-94-1-0995, N00014-94-1-1023 and N00014-96-1-1286 awarded by Office of Naval Research. The United States Government may have certain rights to this invention pursuant to these grants.--

Signed and Sealed this

Twenty-fourth Day of April, 2007

JON W. DUDAS
*Director of the United States Patent and Trademark Office*